(12) United States Patent
Gomez Jimenez et al.

(10) Patent No.: US 7,078,593 B2
(45) Date of Patent: Jul. 18, 2006

(54) SEQUENCE REGULATING THE ANTHER-SPECIFIC EXPRESSION OF A GENE AND ITS USE IN THE PRODUCTION OF ANDROSTERILE PLANTS AND HYBRID SEEDS

(75) Inventors: Maria Dolores Gomez Jimenez, Valencia (ES); Luis Antonio Cañas Clemente, Valencia (ES); Francisco Madueño Albi, Valencia (ES); Jose Pio Beltran Porter, Valencia (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 10/240,299

(22) PCT Filed: Mar. 30, 2001

(86) PCT No.: PCT/ES01/00127

§ 371 (c)(1),
(2), (4) Date: Jan. 28, 2003

(87) PCT Pub. No.: WO01/73088

PCT Pub. Date: Oct. 4, 2001

(65) Prior Publication Data

US 2004/0083504 A1    Apr. 29, 2004

(30) Foreign Application Priority Data

Mar. 31, 2000  (ES) ................................ 200000814

(51) Int. Cl.
*A01H 5/00* (2006.01)
*C12N 15/82* (2006.01)
*C12N 15/11* (2006.01)

(52) U.S. Cl. .................. 800/303; 536/24.1; 435/320.1; 424/93.2; 800/290

(58) Field of Classification Search ................ 800/298, 800/278, 303; 536/24.6; 435/320.1, 419; 424/93.2

See application file for complete search history.

(56) References Cited

U.S. PATENT DOCUMENTS 5,689,041 A * 11/1997 Mariani et al. ............. 800/266

FOREIGN PATENT DOCUMENTS

| EP | 578611 | 1/1994 |
|---|---|---|
| WO | WO 93 25695 | 12/1993 |
| WO | WO 96 26283 | 8/1996 |

OTHER PUBLICATIONS

Maiti et al, 1997, Transgen. Res., 6:143-156.*
Donald et al, 1990, EMBO J. 9:1717-1726.*
Eyal et al, 1995, Plant Cell 7:373-384.*
Chen et al, 2000, Sex. Plant Reprod. 13:85-94.*
Benfrey et al, 1990, Science 250:959-966.*
Kim et al, 1994, Plant Mol. Biol. 24:105-117.*

* cited by examiner

*Primary Examiner*—Anne Kubelik
(74) *Attorney, Agent, or Firm*—Egbert Law Offices

(57) ABSTRACT

The regulatory sequence is useful for the specific expression in anther of a nucleotide sequence of interest, for example, a sequence whose controlled expression under the regulatory sequence causes complete ablation of the anther in the early development stages and allows a user to obtain androsterile plants that are useful for producing hybrid seeds.

10 Claims, 10 Drawing Sheets

```
-2736  gacttcaacc  ttattagtga  atggacaata  aaggttataa  gctcctttac
-2686  tgtgaaagcc  caccagtaac  atcaccttgc  ttatatcatt  cagcttcttt
-2636  ctagtaacat  ttggaacgtg  tttataacag  aaaaaaaccc  aaaaactctg
-2586  aaaagactca  cacttttctt  atctccagtc  cacctctcaa  aaggaacaat
-2536  ttccttcagc  ttcttggttg  gacacctgtt  gagcacatat  gctgcagtgg
-2486  caacagtttc  tccccacaaa  gtgttaggaa  gcttcttctc  cttcagcatg
-2436  ttccttgtca  tatcaagcaa  agttcggttt  tcaacaagac  cattatgttg
-2386  aggagtatat  ggatcagtca  cttcatgctc  aattccattc  tctttacaga
-2336  acttcttgaa  ctctgtagag  ttatactcac  ctccaccatc  agttctgaga
-2286  atcttcagaa  gtctgaccac  tttatttctc  agccttgatt  atgaatttct
-2236  taaattcagc  aaacacctcg  tgtttgaatt  ttataaggga  tacccatgtc
-2186  atccttgtga  actcatccat  aaatgacata  aagtattatt  cctcctagt
-2136  gaaaggtttg  taatgggcca  cacacataag  aatgcactac  tcctaaagca
-2086  tgttttgctc  tttgagctac  ttttgatgaa  aatggcagtc  ttggttgctt
-2036  ccctttcatg  cacacattac  atgactttt  tggtttctta  attgtaggaa
-1986  ttccacgtac  cagtttcttt  gaattcaaat  tccctaagct  cctaaagttc
-1936  aaatgaccaa  atcttttgtt  ccacaactca  ctttccttca  caacacttgt
-1886  tgcgctaagg  cattcagagt  ctgcagtttt  aacattcgcc  ttgaatgttt
-1836  tactccttcc  atgttctgac  tccataatca  acttctgata  acagtcatac
-1786  agcttcaaaa  gaatgtcatt  catggtaact  ggaaatccct  tttcaattaa
-1736  ttgacctaca  ctcatcagat  tgctcttcat  gccaagaacg  taccaagacg
-1686  ttctgaatta  atgcagattt  tctattattc  ataatcactc  taacattccc
-1636  cattccttta  gcatttagtt  acttatcatc  agcacatcta  atcttggttt
-1586  tcttcctaga  gtcaaaatca  accagccatt  tcttatttcc  agtatgatgg
-1536  tttgaacaac  cagtgtccat  atatcaccag  tcttctatag  acgcactatc
-1486  ataactagaa  gccattaata  gcacatgttc  atcatggtgc  tcagatcctt
-1436  agaatgttca  attgctacaa  cgatgtaatc  aaactgatga  gtaagagatc
-1386  taagtacctt  ctcaatgata  ctttcctcat  aaagagtttc  tccatgcgac
-1336  ttcatctcat  ttgtgatcag  aatcactcta  gagatgtagt  cagataactt
-1286  ctcattgttc  ttcatgctta  gattctcata  ctgctcacgt  agagactgaa
-1236  gtttcacctt  ctacactgat  gcatcactat  cgtagcacca  caccagtctg
-1186  tctcacacaa  ccttttccgt  cattgaatca  acgatttct  taaacacgtt
-1136  cacatccaca  cactgatgga  tgtagaacaa  cgcattctga  tccttcttcc
-1086  tcatatcaca  ctgagcattt  ctttgcgcat  ccgttgcatt  ttctagaagt
-1306  gaagcataaa  cttcgttgat  gagatcaaga  acatcttgag  caccaaataa
 -986  cacacacatc  tgaatcatcc  aacgattcca  gttgttgtcg  tcgaacaatg
 -936  gnagcntggt  gcacagattc  acaacgatat  attataantt  ttgttttatg
 -886  aaatttaaga  acaaatttcc  attattctta  aaatgtttac  acactgatgt
 -836  agactgcaaa  aggaataaag  atacaatttg  ttcacaccac  tcacttgcgt
 -786  aaatataagt  gagagttaat  gagaaatact  aaaataccct  ctaaaattat
 -736  gaattaattc  taacaatctc  taatgttagt  ataatccatt  aaacactttg
 -686  atggcaggta  taacaagggt  gtaagttagt  gtatacatat  taggctctta
 -636  ttatttttat  attatctctg  cttttcttct  tcatgttctc  actaatatga
 -586  tattatctcc  cttccctaaa  ttatttatat  ttattagaaa  aagagtttca
 -536  tttttaaaa  atatattacc  gtaattttc  aaaaaataaa  atttaaatat
 -486  attttataaa  aaaattattt  aataatttat  ttacattaat  gcataaatat
 -436  aaataaatac  tgtcatttaa  tatttaacct  tttaacaata  aattatattt
 -386  atttaattca  actaatataa  gctaagttat  ctcatccaac  caattaaaaa
 -336  gatcatttga  aaatacctt   ttatttagtt  tgtggcggtt  tcaactgtca
 -286  aaaaaagga   atttttacga  cgatataaat  ttaaaccagc  aaaaaattga
 -236  agcagttaag  cgaaccaact  catggtatgt  ggatatattt  atctttgtcg
 -186  tttatatcgg  attcgaatct  ctataatgat  gaaaaattaa  tatcaaactt
 -136  taaataagaa  cgtcatttat  agagccattt  tgggaaacac  atatttcatg
  -86  tacacgtgat  tcgcaaattt  ccaataactc  tatatatagc  cctcctcagt
  -36  ttcatgcatt  tgctcacaac  ataaccttcc  ttgaatTCGA  TATCTACCTA
       AGATGACAAA  ACCAGG                                +1
```

FIGURE 2

END1

```
tcgatatctacctaagatgacaaaaccaggttacattaatgctgcttttcgttcatcttt      60
                 M  T  K  P  G  Y  I  N  A  A  F  R  S  S  F      15 caacggcgaacgttacttattcatcgatgataagtatgtgttggtagattatgcaccggg     120
 N  G  E  R  Y  L  F  I  D  D  K  Y  V  L  V  D  Y  A  P  G      35 aacccgcgacgataagctcttaaacgggcctcttcctcttcctgctgggtttaaatcact     180
 T  R  D  D  K  L  L  N  G  P  L  P  L  P  A  G  F  K  S  L      55 tgatggtacagtatttggaacctacggagttgactgtgcctttgacaccgataacgacga    240
 D  G  T  V  F  G  T  Y  G  V  D  C  A  F  D  T  D  N  D  E      75 agcattcatctttatgagaactttactgctctcataaactatgctccacatacttacaa     360
 A  F  I  F  Y  E  N  F  T  A  L  I  N  Y  A  P  H  T  Y  N      95 tgacaaaatcatctcgggtccgaagaaaatctcggacatgtttccttttttcaaaggaac    360
 D  K  I  I  S  G  P  K  K  I  S  D  M  F  P  F  F  K  G  T     115 cgtgtttgaaaacgggattgacgctgcattcaggtcaactaaggagaaagaagtttattt    440
 V  F  E  N  G  I  D  A  A  F  R  S  T  K  E  K  E  V  Y  L     135 attcaaaggagacttgtatgctcgtatagactatggaaaaaactatctggttcaaagtat    480
 F  K  G  D  L  Y  A  R  I  D  Y  G  K  N  Y  L  V  Q  S  I     155 caagaacattagcactgggttcccttgtttcactggaaccgtctttgaaaatggagtgga    540
 K  N  I  S  T  G  F  P  C  F  T  G  T  V  F  E  N  G  V  D     175 tgctgcttttgcttctcacaggaccaatgaagcatacttttcaaaggagattactatgc     600
 A  A  F  A  S  H  R  T  N  E  A  Y  F  F  K  G  D  Y  Y  A     195 acttgtcaagattagcccggggcggaatagatgactatattatcggtggtgtgaagcccat    660
 L  V  K  I  S  P  G  G  I  D  D  Y  I  I  G  G  V  K  P  I     215 tcttgagaattggccttctcttcgtggtataatacctcagaaaagttaaatgtggctctc    720
 L  E  N  W  P  S  L  R  G  I  I  P  Q  K  S  *                  230 tgtgtgtgtgtgatatcatcagtcaagtatggtattaagaataaagactattgttgtcgt    780
tgttgtgtgtttctttttcatgttgtttctagttcttaatgtttgcttatgttgttcatg    840
tgaactatgtaatgacatgcactgtgtacgcgcagagtgaaaataatatattactgtga    900
tgttgattac                                                       910
```

FIGURE 2 (bis)

```
                              -100                         -114
    END1       ⟹      T T T  C C  c A A A A T  G G  c T
                              A        A A A T          A A
Sequence consensus  ⟹   T T    C C           N N    G G
of union of DNA of        T        T t t A              t t
ag                                 ⎵_____⎵
                                         Caja CArG
```

FIG. 3

SEQUENCE LISTING

<160> NUMBER OF SEQ ID NOS: 5

<210> SEQ ID NO 1
<211> LENGTH: 2766
<212> TYPE: DNA
<213> ORGANISM: Pisum sativum
<220> FEATURE:
<221> NAME/KEY: promoter
<222> LOCATION: (1)..(2736)
<223> OTHER INFORMATION:
<220> FEATURE:
<221> NAME/KEY: misc_feature
<222> LOCATION: (1)..(2766)
<223> OTHER INFORMATION: N=Inosine
<220> FEATURE:
<221> NAME/KEY: TATA_signal
<222> LOCATION: (2474)..(2479)
<223> OTHER INFORMATION:
<220> FEATURE:
<221> NAME/KEY: TATA_signal
<222> LOCATION: (2681)..(2688)
<223> OTHER INFORMATION:
<220> FEATURE:
<221> NAME/KEY: CAAT_signal
<222> LOCATION: (2336)..(2339)
<223> OTHER INFORMATION:
<220> FEATURE:
<221> NAME/KEY: CAAT_signal
<222> LOCATION: (2391)..(2394)
<223> OTHER INFORMATION:
<220> FEATURE:
<221> NAME/KEY: CAAT_signal
<222> LOCATION: (2672)..(2675)
<223> OTHER INFORMATION:
<220> FEATURE:
<221> NAME/KEY: C_region
<222> LOCATION: (2408)..(2417)
<223> OTHER INFORMATION:
<220> FEATURE:
<221> NAME/KEY: C_region
<222> LOCATION: (2437)..(2446)
<223> OTHER INFORMATION:
<220> FEATURE:
<221> NAME/KEY: C_region
<222> LOCATION: (2625)..(2634)
<223> OTHER INFORMATION: Complement
<220> FEATURE:
<221> NAME/KEY: GC_signal
<222> LOCATION: (2447)..(2453)
<223> OTHER INFORMATION:
<220> FEATURE:
<221> NAME/KEY: allele
<222> LOCATION: (2610)..(2615)
<223> OTHER INFORMATION:
<220> FEATURE:
<221> NAME/KEY: STS
<222> LOCATION: (2230)..(2236)
<223> OTHER INFORMATION:
<220> FEATURE:
<221> NAME/KEY: STS
<222> LOCATION: (2449)..(2457)
<223> OTHER INFORMATION:
<220> FEATURE:
<221> NAME/KEY: STS
<222> LOCATION: (2490)..(2496)
<223> OTHER INFORMATION:
<220> FEATURE:
<221> NAME/KEY: gene
<222> LOCATION: (2737)..(2766)
<223> OTHER INFORMATION:

<400> SEQUENCE: 1
gacttcaacc ttattagtga atggacaata aaggttataa gctcctttac tgtgaaagcc     60
caccagtaac atcaccttgc ttatatcatt cagcttcttt ctagtaacat ttggaacgtg    120

-continued

```
tttataacag aaaaaaaccc aaaaactctg aaaagactca cactttctt atctccagtc      180 cacctctcaa aaggaacaat ttccttcagc ttcttggttg gacacctgtt gagcacatat     240
gctgcagtgg caacagtttc tccccacaaa gtgttaggaa gcttcttctc cttcagcatg     300
ttccttgtca tatcaagcaa agttcggttt tcaacaagac cattatgttg aggagtatat    360
ggatcagtca cttcatgctc aattccattc tctttacaga acttcttgaa ctctgtagag    420
ttatactcac ctccaccatc agttctgaga atcttcagaa gtctgaccac tttatttctc    480
agccttgatt atgaatttct taaattcagc aaacacctcg tgtttgaatt ttataaggga    540
tacccatgtc atccttgtga actcatccat aaatgacata agtattatt ccctcctagt     600 gaaaggtttg taatgggcca cacacataag aatgcactac tcctaaagca tgttttgctc    660
tttgagctac ttttgatgaa aatggcagtc ttggttgctt ccctttcatg cacacattac    720 atgactttt tggtttctta attgtaggaa ttccacgtac cagtttcttt gaattcaaat     780
tccctaagct cctaaagttc aaatgaccaa atcttttgtt ccacaactca ctttccttca    840
caacacttgt tgcgctaagg cattcagagt ctgcagtttt aacattcgcc ttgaatgttt    900
tactccttcc atgttctgac tccataatca acttctgata acagtcatac agcttcaaaa    960
gaatgtcatt catggtaact ggaaatccct tttcaattaa ttgacctaca ctcatcagat    1020
tgctcttcat gccaagaacg taccaagacg ttctgaatta atgcagattt tctattattc    1080
ataatcactc taacattccc cattccttta gcatttagtt acttatcatc agcacatcta    1140
atcttggttt tcttcctaga gtcaaaatca accagccatt tcttatttcc agtatgatgg    1200
tttgaacaac cagtgtccat atatcaccag tcttctatag acgcactatc ataactagaa    1260
gccattaata gcacatgttc atcatggtgc tcagatcctt agaatgttca attgctacaa    1320
cgatgtaatc aaactgatga gtaagagatc taagtacctt ctcaatgata ctttcctcat    1380
aaagagtttc tccatgcgac ttcatctcat ttgtgatcag aatcactcta gagatgtagt    1440
cagataactt ctcattgttc ttcatgctta gattctcata ctgctcacgt agagactgaa    1500
gtttcacctt ctacactgat gcatcactat cgtagcacca caccagtctg tctcacacaa    1560
ccttttccgt cattgaatca acgatttttct taaacacgtt cacatccaca cactgatgga   1620
tgtagaacaa cgcattctga tccttcttcc tcatatcaca ctgagcattt ctttgcgcat    1680
ccgttgcatt ttctagaagt gaagcataaa cttcgttgat gagatcaaga acatcttgag    1740
caccaaataa cacacacatc tgaatcatcc aacgattcca gttgttgtcg tcgaacaatg    1800
gnagcntggt gcacagattc acaacgatat attataantt ttgttttatg aaatttaaga    1860
acaaatttcc attattctta aaatgtttac acactgatgt agactgcaaa aggaataaag    1920
atacaatttg ttcacaccac tcacttgcgt aaatataagt gagagttaat gagaaatact    1980 aaaatacccct ctaaaattat gaattaattc taacaatctc taatgttagt ataatccatt   2040
aaacactttg atggcaggta taacaagggt gtaagttagt gtatacatat taggctctta    2100 ttattttat attatctctg cttttcttct tcatgttctc actaatatga tattatctcc     2160
cttccctaaa ttatttatat ttattagaaa aagagtttca tttttttaaaa atatattacc   2220 gtaattttc aaaaaataaa atttaaatat attttataaa aaaattattt aataatttat     2280
ttacattaat gcataaatat aaataaatac tgtcatttaa tatttaacct tttaacaata    2340
aattatattt atttaattca actaatataa gctaagttat ctcatccaac caattaaaaa    2400
gatcatttga aaataccttt ttatttagtt tgtggcggtt tcaactgtca aaaaaagga     2460
```

```
atttttacga cgatataaat ttaaaccagc aaaaaattga agcagttaag cgaaccaact    2520
catggtatgt ggatatattt atctttgtcg tttatatcgg attcgaatct ctataatgat    2580
gaaaaattaa tatcaaactt taaataagaa cgtcatttat agagccattt tgggaaacac    2640
atatttcatg tacacgtgat tcgcaaattt ccaataactc tatatatagc cctcctcagt    2700
ttcatgcatt tgctcacaac ataaccttcc ttgaattcga tatctaccta agatgacaaa    2760
accagg                                                                2766

<210> SEQ ID NO 2
<211> LENGTH: 910
<212> TYPE: DNA
<213> ORGANISM: Pisum sativum
<220> FEATURE:
<221> NAME/KEY: CDS
<222> LOCATION: (17)..(706)
<223> OTHER INFORMATION:

<400> SEQUENCE: 2
tcgatatcta cctaag atg aca aaa cca ggt tac att aat gct gct ttt cgt      52
               Met Thr Lys Pro Gly Tyr Ile Asn Ala Ala Phe Arg
                 1               5                  10 tca tct ttc aac ggc gaa cgt tac tta ttc atc gat gat aag tat gtg      100
Ser Ser Phe Asn Gly Glu Arg Tyr Leu Phe Ile Asp Asp Lys Tyr Val
         15                  20                  25 ttg gta gat tat gca ccg gga acc cgc gac gat aag ctc tta aac ggg      148
Leu Val Asp Tyr Ala Pro Gly Thr Arg Asp Asp Lys Leu Leu Asn Gly
     30                  35                  40 cct ctt cct ctt cct gct ggg ttt aaa tca ctt gat ggt aca gta ttt      196
Pro Leu Pro Leu Pro Ala Gly Phe Lys Ser Leu Asp Gly Thr Val Phe
 45                  50                  55                  60 gga acc tac gga gtt gac tgt gcc ttt gac acc gat aac gac gaa gca      244
Gly Thr Tyr Gly Val Asp Cys Ala Phe Asp Thr Asp Asn Asp Glu Ala
                 65                  70                  75 ttc atc ttt tat gag aac ttt act gct ctc ata aac tat gct cca cat      292
Phe Ile Phe Tyr Glu Asn Phe Thr Ala Leu Ile Asn Tyr Ala Pro His
             80                  85                  90 act tac aat gac aaa atc atc tcg ggt ccg aag aaa atc tcg gac atg      340
Thr Tyr Asn Asp Lys Ile Ile Ser Gly Pro Lys Lys Ile Ser Asp Met
         95                 100                 105 ttt cct ttt ttc aaa gga acc gtg ttt gaa aac ggg att gac gct gca      388
Phe Pro Phe Phe Lys Gly Thr Val Phe Glu Asn Gly Ile Asp Ala Ala
    110                 115                 120 ttc agg tca act aag gag aaa gaa gtt tat tta ttc aaa gga gac ttg      436
Phe Arg Ser Thr Lys Glu Lys Glu Val Tyr Leu Phe Lys Gly Asp Leu
125                 130                 135                 140 tat gct cgt ata gac tat gga aaa aac tat ctg gtt caa agt atc aag      484
Tyr Ala Arg Ile Asp Tyr Gly Lys Asn Tyr Leu Val Gln Ser Ile Lys
                145                 150                 155 aac att agc act ggg ttc cct tgt ttc act gga acc gtc ttt gaa aat      532
Asn Ile Ser Thr Gly Phe Pro Cys Phe Thr Gly Thr Val Phe Glu Asn
            160                 165                 170 gga gtg gat gct gct ttt gct tct cac agg acc aat gaa gca tac ttt      580
Gly Val Asp Ala Ala Phe Ala Ser His Arg Thr Asn Glu Ala Tyr Phe
        175                 180                 185 ttc aaa gga gat tac tat gca ctt gtc aag att agc ccg ggc gga ata      628
Phe Lys Gly Asp Tyr Tyr Ala Leu Val Lys Ile Ser Pro Gly Gly Ile
    190                 195                 200 gat gac tat att atc ggt ggt gtg aag ccc att ctt gag aat tgg cct      676
Asp Asp Tyr Ile Ile Gly Gly Val Lys Pro Ile Leu Glu Asn Trp Pro
205                 210                 215                 220
```

-continued

```
tct ctt cgt ggt ata ata cct cag aaa agt taaatgtggc tctctgtgtg       726
Ser Leu Arg Gly Ile Ile Pro Gln Lys Ser
                225                 230 tgtgtgatat catcagtcaa gtatggtatt aagaataaag actattgttg tcgttgttgt   786
gtgtttcttt ttcatgttgt ttctagttct taatgtttgc ttatgttgtt catgtgaact   846
atgtaatgac atgcactgtg tacgcgcaga gtgaaaataa tatattactg tgtatgttga   906
ttac                                                                910
```

<210> SEQ ID NO 3
<211> LENGTH: 230
<212> TYPE: PRT
<213> ORGANISM: Pisum sativum

<400> SEQUENCE: 3

```
Met Thr Lys Pro Gly Tyr Ile Asn Ala Ala Phe Arg Ser Ser Phe Asn
1               5                   10                  15

Gly Glu Arg Tyr Leu Phe Ile Asp Asp Lys Tyr Val Leu Val Asp Tyr
                20                  25                  30

Ala Pro Gly Thr Arg Asp Asp Lys Leu Leu Asn Gly Pro Leu Pro Leu
            35                  40                  45

Pro Ala Gly Phe Lys Ser Leu Asp Gly Thr Val Phe Gly Thr Tyr Gly
        50                  55                  60

Val Asp Cys Ala Phe Asp Thr Asp Asn Asp Glu Ala Phe Ile Phe Tyr
65                  70                  75                  80

Glu Asn Phe Thr Ala Leu Ile Asn Tyr Ala Pro His Thr Tyr Asn Asp
                85                  90                  95

Lys Ile Ile Ser Gly Pro Lys Lys Ile Ser Asp Met Phe Pro Phe Phe
            100                 105                 110

Lys Gly Thr Val Phe Glu Asn Gly Ile Asp Ala Ala Phe Arg Ser Thr
        115                 120                 125

Lys Glu Lys Glu Val Tyr Leu Phe Lys Gly Asp Leu Tyr Ala Arg Ile
    130                 135                 140

Asp Tyr Gly Lys Asn Tyr Leu Val Gln Ser Ile Lys Asn Ile Ser Thr
145                 150                 155                 160

Gly Phe Pro Cys Phe Thr Gly Thr Val Phe Glu Asn Gly Val Asp Ala
                165                 170                 175

Ala Phe Ala Ser His Arg Thr Asn Glu Ala Tyr Phe Phe Lys Gly Asp
            180                 185                 190

Tyr Tyr Ala Leu Val Lys Ile Ser Pro Gly Gly Ile Asp Asp Tyr Ile
        195                 200                 205

Ile Gly Gly Val Lys Pro Ile Leu Glu Asn Trp Pro Ser Leu Arg Gly
    210                 215                 220

Ile Ile Pro Gln Lys Ser
225                 230
```

<210> SEQ ID NO 4
<211> LENGTH: 230
<212> TYPE: PRT
<213> ORGANISM: Pisum sativum

<400> SEQUENCE: 4

```
Met Thr Lys Pro Gly Tyr Ile Asn Ala Ala Phe Arg Ser Ser Phe Asn
1               5                   10                  15

Gly Glu Arg Tyr Leu Phe Ile Asp Asp Lys Tyr Val Leu Val Asp Tyr
                20                  25                  30
```

-continued

```
Ala Pro Gly Thr Arg Asp Asp Lys Leu Leu Asn Gly Pro Leu Pro Leu
         35                  40                  45
Pro Ala Gly Phe Lys Ser Leu Asp Gly Thr Val Phe Gly Thr Tyr Gly
     50                  55                  60
Val Asp Cys Ala Phe Asp Thr Asp Asn Asp Glu Ala Phe Ile Phe Tyr
 65                  70                  75                  80
Glu Asn Phe Thr Ala Leu Ile Asn Tyr Ala Pro His Thr Tyr Asn Asp
                 85                  90                  95
Lys Ile Ile Ser Gly Pro Lys Lys Ile Ser Asp Met Phe Pro Phe Phe
                100                 105                 110
Lys Gly Thr Val Phe Glu Asn Gly Ile Asp Ala Ala Phe Arg Ser Thr
            115                 120                 125
Lys Glu Lys Glu Val Tyr Leu Phe Lys Gly Asp Leu Tyr Ala Arg Ile
        130                 135                 140
Asp Tyr Gly Lys Asn Tyr Leu Val Gln Ser Ile Lys Asn Ile Ser Thr
145                 150                 155                 160
Gly Phe Pro Cys Phe Thr Gly Thr Val Phe Glu Asn Gly Val Asp Ala
                165                 170                 175
Ala Phe Ala Ser His Arg Thr Asn Glu Ala Tyr Phe Phe Lys Gly Asp
                180                 185                 190
Tyr Tyr Ala Leu Val Lys Ile Ser Pro Gly Gly Ile Asp Asp Tyr Ile
            195                 200                 205
Ile Gly Gly Val Lys Pro Ile Leu Glu Asn Trp Pro Ser Leu Arg Gly
        210                 215                 220
Ile Ile Pro Gln Lys Ser
225                 230
```

<210> SEQ ID NO 5
<211> LENGTH: 1561
<212> TYPE: DNA
<213> ORGANISM: Pisum sativum
<220> FEATURE:
<221> NAME/KEY: promoter
<222> LOCATION: (1)..(1561)
<223> OTHER INFORMATION:
<220> FEATURE:
<221> NAME/KEY: misc_feature
<222> LOCATION: (1)..(1561)
<223> OTHER INFORMATION: N= Inosine

<400> SEQUENCE: 5

```
acaaccagtg tccatatatc accagtcttc tatagacgca ctatcataac tagaagccat      60
taatagcaca tgttcatcat ggtgctcaga tccttagaat gttcaattgc tacaacgatg     120
taatcaaact gatgagtaag agatctaagt accttctcaa tgatactttc ctcataaaga     180
gtttctccat gcgacttcat ctcatttgtg atcagaatca ctctagagat gtagtcagat     240
aacttctcat tgttcttcat gcttagattc tcatactgct cacgtagaga ctgaagtttc     300
accttctaca ctgatgcatc actatcgtag caccacacca gtctgtctca cacaaccttt     360
tccgtcattg aatcaacgat tttcttaaac acgttcacat ccacacactg atggatgtag     420
aacaacgcat tctgatcctt cttcctcata tcacactgag catttctttg cgcatccgtt     480
gcattttcta gaagtgaagc ataaacttcg ttgatgagat caagaacatc ttgagcacca     540
aataacacac acatctgaat catccaacga ttccagttgt tgtcgtcgaa caatggnagc     600
ntggtgcaca gattcacaac gatatattat aanttttgtt ttatgaaatt taagaacaaa     660
tttccattat tcttaaaatg tttacacact gatgtagact gcaaaggaa taaagataca      720
```

```
                                                  -continued atttgttcac accactcact tgcgtaaata taagtgagag ttaatgagaa atactaaaat    780
accctctaaa attatgaatt aattctaaca atctctaatg ttagtataat ccattaaaca    840
ctttgatggc aggtataaca agggtgtaag ttagtgtata catattaggc tcttattatt    900
tttatattat ctctgctttt cttcttcatg ttctcactaa tatgatatta tctcccttcc    960
ctaaattatt tatatttatt agaaaaagag tttcattttt taaaaatata ttaccgtaat   1020
ttttcaaaaa ataaaattta aatatatttt ataaaaaaat tatttaataa tttatttaca   1080
ttaatgcata aatataaata aatactgtca tttaatattt aaccttttaa caataaatta   1140
tatttattta attcaactaa tataagctaa gttatctcat ccaaccaatt aaaaagatca   1200
tttgaaaata ccttttattt tagtttgtgg cggtttcaac tgtcaaaaaa aaggaatttt   1260
tacgacgata taaatttaaa ccagcaaaaa attgaagcag ttaagcgaac caactcatgg   1320
tatgtggata tatttatctt tgtcgttttat atcggattcg aatctctata atgatgaaaa   1380
attaatatca aactttaaat aagaacgtca tttatagagc cattttggga aacacatatt   1440
tcatgtacac gtgattcgca aatttccaat aactctatat atagccctcc tcagtttcat   1500
gcatttgctc acaacataac cttccttgaa ttcgatatct acctaagatg acaaaaccag   1560
g                                                                  1561
```

SEQUENCE REGULATING THE ANTHER-SPECIFIC EXPRESSION OF A GENE AND ITS USE IN THE PRODUCTION OF ANDROSTERILE PLANTS AND HYBRID SEEDS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

Agriculture. The present invention is related with the obtention of regulating DNA sequences (promoters) and, using said sequences, with the construction of new chimeric genes able to be specifically expressed in the anthers of transgenic plants. The invention also relates to the production of androsterile plants and hybrid seeds.

BACKGROUND OF THE INVENTION

To provoke the specific expression of certain genes in the anthers of transgenic plants, different promoters have been isolated, characterised and used. The expression of these promoters is specific to a given tissue of the anther. Some of them have been used in cell ablation techniques to produce sterile plants of great utility for the production of hybrid seeds. Currently, genetic ablation of plant cells is being used to carry out studies of cell functioning and signalling within specific organs or tissues and to generate androsterility (male-sterility).

Genetic ablation is based on the induction of cell death by means of the expression of any enzyme that is able to destroy cell integrity such as proteases, lipases and RNases (for example, barnase and T1 RNase). Equivalent results can be obtained by expressing toxic substances into the cells [Day C D and Irish V F. Trends Plant Sci., 2: 106–111, 1997]. An example of this last method is the use of peptides that deactivate ribosomes, as is the case of the A chain of the toxin from *Corynebacterium diphtheria* (DTA) and the exotoxin A from *Pseudomonas aeruginosa*. Several groups have suggested the production of androsterility via overproduction of growth regulators. The synthesis of auxins and cytokinines using genes of non-plant origin, such as genes 1 and 2 of the Ti plasmid, or the genes rol A, B and C of the plasmid Ri, represent methods where these factors become toxins due to the magnitude and inappropriate moment of expression.

Methods have also been developed that do not directly destroy the tissue, but rather give rise to cells susceptible to specific ablative agents. An example of this approach is the use of an "antisense" RNA from a previously established gene. This confers inherited resistance to a chemical agent, such as, for example, tolerance to a herbicide (Fabijanski SF et al., In vitro Cell. Dev. Biol. 28: 46–52, 1992]. The effect of the "antisense" RNA is to specifically eliminate the chemical resistance, for example, in pollen, so that the application of the herbicide leads to destruction of the pollen. This method converts a herbicide into a gametocide.

In order to obtain an efficient genetic ablation, it is crucial to have a cytotoxic gene that acts only where it is expressed and to have an appropriate promoter that controls the spatial-temporal expression of the cytotoxic gene. For this reason, the characterisation of active gene promoters in different cell types and/or at different moments during differentiation of the anther has allowed to examine the functions of different tissues of the anther during the gametogenesis by means of cell ablation [Mariani C et al. Nature, 347: 737–741, 1990; Paul W et al., Plant Mol. Biol., 19: 611–622, 1992; Hird D L et al., Plant J., 4: 1023–1033, 1993], with particular emphasis on the cell to cell interactions [Roberts M R et al., Sex. Plant Reprod., 8: 299–307, 1995]. Similarly, this technique is being used by large seed producing companies for the development of androsterility, a desirable feature in the processes for obtaining hybrid seeds [Williams M E, Trends Biotechnol., 13: 344–349, 1995].

In several works, the function of cell to cell interactions has been analysed during the development of the reproductive structures. For example, several different promoters have been used to direct the expression of a cytotoxic gene in cells from tapetum in the anther with the object of determining the effect of ablation on the development of pollen [Mariani C et al., Nature 347: 737–741, 1990; Roberts M R et al., Sex. Plant Reprod. 8:299–307, 1995]. Ablation of tapetal cells in different studies has different effects on the development of pollen. The use of a specific promoter of tobacco tapetal cells (TA29) directing the expression of the barnase gene (ribonuclease) during the tetrad phase of the pollen development leads to androsterility, which indicates that the tapetum is essential for the production of viable pollen at this stage (Mariani C et al., Nature 347: 737–741, 1990). On the contrary, the substitution of the TA29 promoter by the APG promoter from *Arabidopsis*, specific to tapetur in the microspore phase of pollen, does not have any effect on the pollen [Roberts M R et al., Sex. Plant Reprod. 8:299–307, 1995]. This latter datum indicates that the tapetum is not essential for the formation of pollen from the disintegration of the microspore tetrads. A histochemical analysis of the anther development in transgenic plants of *Brassica* with the TA29-barnase construct showed the degradation of RNA within the tapetal cells along with the disappearance of RNA from the microspores [De Block M and Debrouwer D, Planta 189: 218–225, 1993]. This observation suggests that the microspores remain permeable to small molecules after initiation of the deposition of sporopollenine and in late phases of their development, since the TA29 promoter does not direct the expression of genes in microspores.

Beals T P and Goldberg R B [Plant Cell, 9: 1527–1545, 1997] put into practice a new cell ablation strategy for determining what cell types from an anther are implicated in the dehiscence process. They transformed tobacco plants with two constructs: the construct formed by the TA56 promoter, active in the septum, in the stomium and in the connective tissue, and the barnase gene along with one of the following constructs in an alternative form: a) the TP12 promoter, active in most of the tissues of the anther, along with the barstar gene (barnase inhibitor), b) the TA20 promoter, active in most of the tissues of the anther but with a different distribution pattern from that of TA12, and the barstar gene and c) the soybean lectin gene promoter, active in the cells of the connective tissue, the septum and the stomium, in addition to the barstar gene. The analysis of the different phenotypes of the transgenic plants showed that the dehiscence process only depends on the presence of a functional stomium.

Shull [J. Ind. Abst. Vererb. 12: 97–149, 1914] was the first one to introduce the term heterosis to describe the advantages offered by heterozygosis regarding cell division, growth and other physiological activities of an organism. The result of these advantages: increase in size, vigour, yield, an earlier fructification and resistance to diseases has for some decades induced the attempts to obtain hybrid varieties [Tsaftaris S A, Physiol. Plantarum 94: 362–370, 1995]. Most plants containing both male and female reproductive organs self-pollinate themselves (corn, rice, soybean, tomato, etc.), which causes problems in the processes for producing hybrid seeds [Kriete G et al., Plant J. 9: 809–818, 1996]. To avoid this problem, a system has to be used that controls the self-pollination. This system may be mechanical, chemical or genetic.

The mechanical system consists of manually eliminating the anthers from flowers (emasculation), which is an arduous and expensive task.

The chemical method is based on the use of chemical products (gametocides) that specifically destroy the pollen leading to transitory androsterility. This approximation is not particularly effective in cultures with a long blooming period or with variable or uncontrollable blooming conditions. In addition, the commercial production of hybrid cells via gametocides is characterised by being expensive and by the high relative effectiveness of the chemical products.

Most commercial systems for the production of hybrid seeds are based on genetic methods to control the blooming, so that mutually incompatible plants or androsterile plants are used, that is, plants that do not produce pollen, are unable to release the pollen or develop pollen that is unable to product self fertilisation [Homer H T and Palmer R G, Crop Sci. 35: 1527–1535, 1995]. The production of androsterile plants is of great utility for obtaining hybrid seeds. The male sterility eliminates the possibility of self-fecundation of the plant, thus facilitating the production of hybrids that find important applications in the genetic improvement programmes.

The methods for obtaining hybrid seeds described up until now have limitations and are not applicable in important cultures of agricultural interest. Currently, new strategies are being developed based on genetic engineering to produce androsterile plants [Gates P, Biotechnol. Genet. Engineering Rev. 13: 181–195, 1994]. The development of methods based on recombinant DNA and the characterisation of genes implicated in the development of pollen has allowed the proliferation of molecular systems that provoke nuclear male sterility (NMS), [Scott R J et al., Plant Sci. 80: 167–191, 1991]. As has already been mentioned, the androsterility in molecular systems is achieved by means of cell ablation processes preventing the development of the microspores or the tissues that lead to their development (tapetum and walls of the pollen sacs). In addition, it is possible to produce completely functional pollen, but this pollen is not released due to defects in the structure of the anther. To obtain androsterile plants useful in the production of hybrid seeds it is important to have a specific promoter for the tissues implicated in the development of the pollen, a system for selecting the androsterile line and a system for restoring the fertility in the F1 hybrid line.

Specific Promoters

The transcription process in most plant genes is controlled both temporally and spatially. The regulation of genetic activity is mediated by the interaction between trans factors and cis regulatory elements present in the promoter region of the gene. Thus, a promoter is a DNA sequence that directs the transcription of a structural gene and therefore is located in its 5' region.

The genes that are exclusively expressed in the reproductive organs of the flower (stamen and carpels) are particularly interesting, as their promoters would potentially be able to direct the expression of other genes towards said organs and provoke male or female sterility in the flower. This is the case in some gene promoters that are specifically expressed in the anthers, which have already been used, in combination with ablative agents that only affect the developing pollen, in biotechnological approaches that aim to produce androsterile plants unable to self-pollinate. Therefore, these types of approach greatly depend on the existence of promoters providing a suitable expression. During the last years, numerous genes have been isolated and characterised that are specifically expressed in tissues and cells related to the development of pollen, therefore, promoters are available for this end [Scott R J et al., Plant Sci. 80: 167–191, 1991].

The promoters that are selected for expressing toxic agents or those that are degenerative for the tissue are usually promoters regulated by development, sufficiently active and specific for the target cells. If the target cell is tapetal tissue, the promoter should be active early in the development of the microspore in order to halt the process before the microspores become independent from the support of the tapetum. Similarly, the promoter should act before meiotic segregation to prevent the lack of degenerative activity in part of the microspores if the lethal gene is hemizygotic.

An alternative use of promoters regulated by development is the use of inducible promoters. However, the number of described promoters showing specific chemical induction is very small. The use of an inducible promoter for blocking the development of pollen has advantages when it comes to maintaining and increasing the female line because the plants are fertile and can be multiplied by self-crossing. Inherited active or inducible promoters can also be used if the androsterility is based on the suppression of a gene that is expressed in a tissue implicated in the development of pollen, for example, via "antisense".

Selection of the Androsterile Line.

In order to produce hybrid seeds in industrial quantities it is necessary to increase the female line. Although it is possible to produce many androsterile plants by means of in vitro propagation, for the plants of agricultural interest, this would be too expensive. A common strategy for multiplying the androsterile line is to join a gene that confers resistance to a herbicide to the ablative gene [Mariani C et al., Nature 357: 384–387, 1992]. After crossing the androsterile line with an isogenic and fertile line, the plants that have not inherited the sterility are eliminated by the herbicide. By analogy, any gene allowing discrimination between the two phenotypes could be used, such as for example those affecting the pigmentation of the seeds.

Restoring Fertility

The restoration of fertility in hybrid plants can be carried out by crossing them with transgenic lines expressing an inhibitor specific to the toxic enzyme used for producing the androsterility, as is the case for the barstar gene, the product of which inhibits the action of barnase [Mariani C et al., Nature 357: 384–387, 1992] or an "antisense" RNA of the lethal gene used [Schmülling T et al., Mol. Gen. Genet. 237: 385–394, 1993].

Molecular Systems Used for Obtaining Androsterile Plants

The first ablation strategy designed for producing androsterility was proposed by Mariani et al. [Nature 347: 737–741, 1990]. The promoter of the TA29 tobacco gene, specific to tapetum, was used for directing the expression of two different RNases (T1 Rnase from *Aspergillus oryzae* and barnase from *Bacillus amyloliquefaciens*) in tobacco and *Brassica napus*. The obtained androsterile transgenic anthers lacked the tapetum and contained the pollen sacs with no microspores or pollen grains. The TA29-barnase construct was fused with the bar gene, a gene that confers tolerance to the ammonium gluphosinate herbicide, to allow selection of the androsterile plants in a population. The application of the herbicide to the progeny of a cross eliminates the fertile male plants and thus increases the efficiency with which the sterile plants can be isolated. Despite all this, these transgenic plants were no better than the spontaneous mutants if there was no possibility of reversing the androsterility. Mariani et al. [Nature 357: 384–387, 1992] solved this problem with the production of transgenic plants with a construct containing the inhibitor gene of ribonuclease barnase (barstar) under the control of the TA29 promoter. The TA29-barstar plants act as a restoring line and androfertile plants are obtained when they are crossed with plants transformed with the TA29-barnasa construct.

Apart from this system, the literature contains other methods for producing androsterile lines:

In *Petunia hybrida*, the nuclear androsterility was provoked by suppressing the synthesis of flavonoids in the anther, which prevents the maturation of the pollen. This was achieved in two different ways: through the "antisense" effect of RNA [van der Meer I M et al., Plant Cell 4: 253–262, 1992] and through a co-suppression [Taylor L P and Jorgensen R, J. Hered. 83: 11–17, 1992] of the chalconsynthetase gene, an enzyme implicated in the synthesis route of flavonoids. To restore fertility, flavonoids can be applied to the stigma or mixed with the pollen to allow the androsterile line to multiply by self pollination and therefore, homozygotic lines are obtained for the androsterile phenotype not requiring the use of any marker for selection [Ylstra B et al., Plant J. 6: 201–212, 1994].

In tobacco, the androsterility has also been induced by the expression of the gene rol C of *Agrobacterium rhizogenes* fused with the promoter CaMV 35S. Unfortunately, the androsterile phenotype was accompanied by other phenotypic alterations in the transgenic plant [Schmülling T et al., EMBO J. 7: 2621–2629, 1988]. The restoration of sterility was carried out by expression of an "antisense" RNA of the gene rol C in the F1 hybrids [Schmülling T et al., Mol. Gen. Genet. 237: 385–394, 1993].

O'Keefe et al. [Plant Physiol. 105: 473–482, 1994] described a system of inducible androsterility based on the expression of the $P450_{SU1}$ cytochrome in tobacco tapetal cells. This protein is able to transform an inoffensive derivative of the R7402 gametocide, exogenously added, into its active form (500 times more toxic). However, possibly due to the fast metabolism of R7402, the androsterility is limited to flowers in a certain phase of development during the application of the compound. In addition, R7402 is itself toxic and begins to inhibit growth when it is applied in quantities four times greater than those used to produce androsterility in the classical way.

Another system for obtaining inducible androsterility is based on the use of the TA29 promoter of tapetum along with the argE gene from *E. coli*. The product of this gene deacetylises the N-acetyl-L-phosphinotrycin compound and transforms it into gluphosinate, a cytotoxic compound. When the N-acetyl-L-phosphinotrycin is applied to the tobacco plant, the tapetum degenerates and androsterile plants are obtained [Kriete G et al., Plant J. 9: 809–818, 1996]. Finally, we would like to point out that androsterility, in addition to being an important tool for obtaining hybrids, is also a desirable feature in plants capable to develop fruits in the absence of fertilisation (partenocarpic fruits). In this type of fruit, the seeds are absent and so the consumption or acceptance thereof by the consumers is increased [Rotino G et al., Nat. Biothecnol. 15: 1398–1401,1997]. Some partenocarpic cultures of agricultural interest are: pears, citric fruits, cucumber, grape and dates.

BRIEF SUMMARY OF THE INVENTION

In general, the invention addresses the problem of developing a system useful for producing androsterility in plants.

The solution provided by this invention is based on the isolation and characterisation of a promoter able to direct the specific anther expression in early development phases of the plant, in particular, the END1 gene promoter from pea (*Pisum sativum* L.). The use of said promoter allows to produce transgenic plants that express a gene specific to the anther, for example, a gene that provokes the ablation of the anther and therefore gives rise to an androsterile plant, of greater use in genetic improvement programmes for obtaining hybrid seeds. In Example 1, the production of transgenic plants containing different constructions comprising the END1 promoter fused to a reporter gene is described, observing its specificity on directing the expression of the reporter genes in anthers. Example 2 describes the production of androsterile plants of *Arabidopsis thaliana* by using the barnase gene through the END1 promoter. The obtained results show that said construct provokes the complete ablation of anthers from very early stages in their development, preventing the formation of pollen therein and leading to male sterility of the plant with a 100% effectiveness.

Accordingly, an object of this invention is a sequence of nucleotides regulating the specific expression in the anther of a gene comprising the nucleotide sequence shown in SEQ ID NO 1, or a fragment thereof, or a nucleotide sequence substantially homologous to said sequences. The use of said nucleotide sequence for the production of androsterile plants and hybrid seeds constitutes an additional object of this invention.

Another additional object of this invention constitutes a DNA construct comprising the whole or part of said nucleotide sequence, as well as a vector containing said sequence or DNA construct and a cell transformed with said vector.

Another additional object of the invention constitutes the use of said DNA sequence, or of said DNA construct, in the production of transgenic plants that specifically express in anthers a DNA sequence of interest, for example, transgenically androsterile plants that express a cytotoxic polypeptide or RNA, the expression of which induces the ablation of the anther. The resulting transgenic plants constitute another additional object of this invention.

Another additional object of this invention constitutes a method for producing hybrid seeds comprising introducing into said DNA construct into a plant.

BRIEF DESCRIPTION OF THE SEVERAL VIEWS OF THE DRAWINGS

FIG. 2 shows the sequence of the promoter region of END1. The known motifs, including two possible TATA boxes (tataaat and tatatata), a CAAT box and two CCAAT boxes appear underlined, contained in the Sequence Listing as SEQ. I.D. NO. 1, at 2390 and 2371, and SEQ. I.D. NO. 1 at 2336 for the CAAT box. In blue, three possible CarG boxes are represented, in green a GTCAAAA (SEQ. I.D. NO. 1 at 2447) motif, an element ACGTCA (SEQ. I.D. NO. 1 at 2610) in pink and three motifs $C(A)_{6/8}$ in red. The GTCAAAA (SEQ. I.D. NO. 1 at 2447) box shares its last five nucleotides with one of the boxes $C(A)_{6/8}$. The annotation +1 indicates the cDNA sequence of the clone 162. The translation initiation codon (ATG) is shown in boldface. In addition, there is shown the deduced amino acid sequence. The nucleotides in boldface indicate the codon for stopping translation (taa) and the possible signal of polyadenylation (aataaa).

FIG. 3 shows the stacking of the consensus sequence of joining to DNA of AGAMOUS (CArG box and adjoining sequences) with a putative equivalent sequence found in the promoter region of END1. The sequences shown in FIG. 3 are comprised of SEQ. I.D. NO. 1 at 2434, corresponding generally to $^{-103}$CCCAAAATGG$^{-112}$ compared to a prior art motif disclosed in the prior art article: Huang, H., Mizukami Y., Ma, H. 1993. Isolation and characterization of the binding sequences for the product of the *Arabidopsis* floral homeotic genes agamous. *Nucleic Acid Res.* 21, 4769–4776).

FIG. 10 shows the result of histochemical studies in paraffin sections of the structures formed in place of the anthers in transgenic plants bearing the pEND1-barnase construct. a: Longitudinal section of a control flower of

Figure 1:
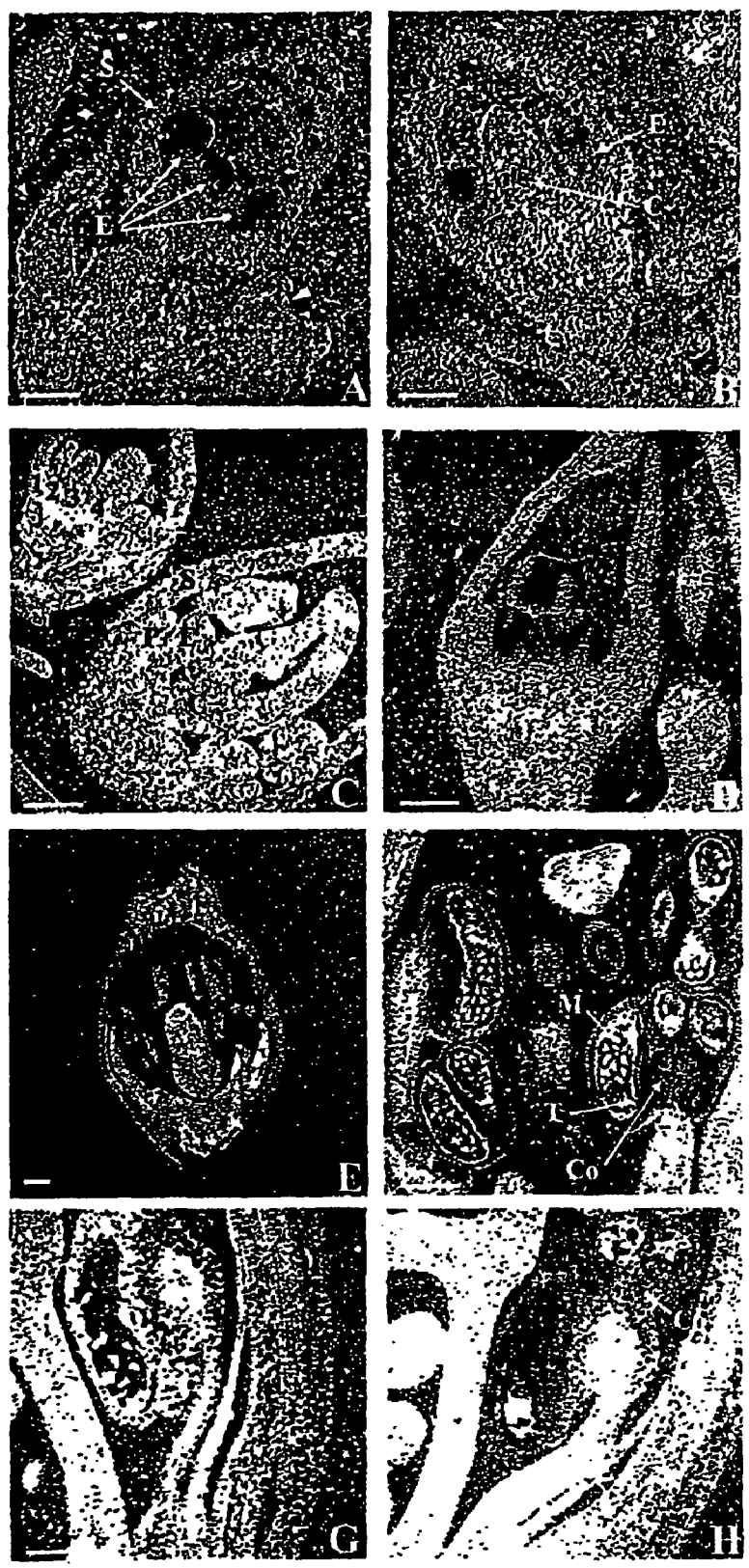
FIG. 1 shows the space-temporal analysis of the expression of END1 in longitudinal sections of pea flowers in different phases. The purple coloured precipitate indicates the site of expression. A. Floral shoot in which the common primordia (s) have still not differentiated into petaloid and staminal features along with a flower on day 12 before the anthesis where the END1 begins to be expressed. B. Flower on day 10 before anthesis. C. Control of the in situ hybridisation: sections hybridised with "sense" riboprobe. D. Flower on day 8 prior to anthesis. E and F. Flowers on day 6 prior to anthesis photographed with smaller and greater magnification, respectively. G and H. Serial sections from a flower on day 5 prior to anthesis hybridised with the "sense" riboprobe (control) and "antisense" riboprobe, respectively. C, carpel; E, stamens; P, petals; Co, connective tissue; M, microspores; T, tapetum; 1, 2, 3 and 4, whorls 1, 2, 3 and 4 of the flower.

*Arabidopsis* in an early development stage of the anther. In red, a group of mother cells of the microspores can be seen that will give rise to the mature pollen after successive divisions. b: Control anther in a more advanced developmental stage (12–13, before dehiscence) in which the almost complete disappearance of the tapetum can be observed and the pollen is found in a maturing process (red). The filament has begun to lengthen. c and d: Longitudinal sections of two transgenic flowers in stage 13 and 12 respectively, in which the structures formed in place of the stamens are observed. Inside the widening produced in the terminal zone, a small group of pollen mother cells is observed and maybe someone of the external tapetum (red) that have stopped their development (there are no divisions). The filament has not begun to lengthen. e: Detail of one of the structures shown in figure d where detail is shown of the group of round pollen mother cells and possible tapetal cells.

DETAILED DESCRIPTION OF THE INVENTION

The invention provides a sequence of nucleotides regulating the specific expression in the anther of a gene, hereinafter the nucleotide sequence of the invention, selected from:
 a) A nucleotide sequence comprising the nucleotide sequence shown in SEQ ID NO 1;
 b) A fragment of said SEQ ID NO 1 retaining its capacity to regulate specific expression in the anther; and
 c) A nucleotide sequence that is substantially analogous to the sequence of nucleotides defined in a) or in b).

In the sense used in this description, the term "analogous" is to include any sequence of nucleotides having at least capacity to regulate specific expression in the anther. Typically, the analogous DNA sequence:
 Can be isolated from any organism producing said analogous sequence based on the nucleotide sequence shown in SEQ ID NO 1, or
 It is constructed on the basis of the nucleotide sequence shown in SEQ ID NO. 1 by means of substitution of one or more nucleotides, the insertion of one or more nucleotides in the sequence, the addition of one or more nucleotides at either end of the sequence, or the deletion of one or more nucleotides at either end or in the inner part of the sequence. For example, the analogous DNA sequence can be a subsequence of the nucleotide sequence shown in SEQ ID NO 1.

In general, the analogous DNA sequence is substantially homologous to the nucleotide sequence identified as SEQ ID NO 1. In the sense used in this specification, the expression "substantially homologous" means that at a nucleotide level the nucleotide sequences in question have an identity degree of at least 60%, preferably at least 85%, or more preferably at least 95%.

The nucleotide sequence of the invention can originate from any organism that contains it, for example, from pea (*Pisum sativum* L.) or from a host organism transformed with said DNA sequence. The nucleotide sequence of the invention can be isolated by means of conventional techniques, starting from the DNA from any other species by employing oligonucleotide probes prepared from information on the nucleotide sequence of the invention.

In a particular embodiment, the nucleotide sequence of the invention is the sequence shown in SEQ ID NO 1, corresponding to the nucleotide sequence of the promoter of the END1 gene of pea (*Pisum sativum* L.).

In previous works carried out in our laboratory, we isolated and characterised a gene of the pea (*Pisum sativum* L.) that was exclusively expressed in certain tissues of the anthers. Its isolation and characterisation was carried out by means of the prior purification and identification of the protein it codes. To do this, a process of immunosubtraction of extracts from stamens was carried out with polyclonal serum obtained by immunisation of a rabbit with extracts from the other floral organs (sepals, petals and carpels). The result of this process was the production of an extract enriched in proteins specific to the stamens, eliminating those that these organs have in common with the remaining floral organs. Said enriched extract was used to immunise mice and obtain hybridoma lines that produced monoclonal antibodies specific for a certain staminal protein. One of those (MAbA1) recognised a protein of 26 kDa (END1) present in much abundance in the stamens extracts and whose immunolocalisation indicated to us that it accumulated exclusively in the tissues that make up the architecture of the pollen sacs of the anther. Using affinity chromatography, we purified a certain amount of said protein and sequenced 20 aas of its N-terminus. The obtained sequence had a high homology with another protein (PA2) previously described in pea cotyledons and whose function is unknown [Higgins et al., Plant Mol. Biol. 8: 37–45, 1987]. The use of the cDNA of PA2 as a probe in the screening of a gene library of pea flowers allowed us to isolate a clone with the complete coding sequence (910 bp, which we call END1, SEQ ID NO 2), which shows 72% homology with that of PA2. The Northern Blot assays showed the specificity of expression of this new protein as it was restricted to anther extracts and was not detected in other floral organs, cotyledons and plant tissues. On the other hand, the in situ hybridisation assays corroborated the specificity of the expression of the END1 gene in the anther tissues of the pea during the different developmental phases (FIG. 1). Its expression started in early developmental phases (differentiation of the common primordia cells in petals and stamens) and continued until the dehiscence of the anther, being expressed only in the epidermis, connective tissue, middle layer and endothecium. Expression of the gene was not detected in the nutritive tissue (tapetum) or in the germinal tissue (pollen). The assays carried out with other floral organs, other parts of the plant (stem, leaves, roots, etc.) or with seeds (cotyledons) were negative.

The specific expression of the END1 gene in those tissues that form the pollen sacs of the anthers suggested to us the isolation and analysis of the promoter of said gene. The study of this promoter was interesting for different reasons. First, we could determine which motifs of a promoter determine the specific expression of a gene in the anther. Similarly, it would be interesting to analyse what transcriptional factors regulate the expression of the END1 gene and to determine whether these are related to the MADS-box homeotic genes which regulate the identity of the floral organs, in particular, with genes of class B and C that are implicated in the development of stamens. With these objectives, we examined a genomic DNA library of the pea, using the complete fragment of the END1 cDNA (SEQ ID NO 2) as a probe. An initial examination was carried out with 500,000 phage plaques in which we found a positive clone (clone 162). This was purified and isolated after three more examinations. By means of the culture and positive phage lysis we purified its DNA. This DNA was digested with HindII, as this enzyme spliced the fragment of cDNA at 210 bp from its start and from the phage digestion we could obtain a DNA fragment containing the first 210 bp of cDNA plus more promoter sequences upstream from these. With the digested DNA, a Southern Blot analysis was carried out using the 210 bp of the 5' terminus of the cDNA fragment of the clone 162 as a probe to hybridise. This fragment was used as a probe to determine which fragment resulting from the restriction would be the one constituted by these 210 bp and part or all of the promoter sequence. The Southern Blot analysis showed that a fragment of approximately 3 Kb derived from the digestion of phage DNA with HindII hybridised with the probe. The fragment of 3 Kb was purified using the QUIAEXII method, cloning in the Bluescript-KS(−) vector at the HindII site of the cloning site and subsequently sequenced. The complete nucleotide sequence of the END1 promoter is represented in FIG. 2 and in SEQ ID NO 1 (the nucleotides from −2736 and 1 of FIG. 2 correlate with the nucleotides 1 and 2766 of SEQ ID NO 1, respectively).

After sequencing the cloned fragment, we observed that we have isolated a fragment of 2946 bp. Of these, the 210 bp of the 3' terminus corresponded to the first 210 bp of the fragment of the clone of cDNA 162. At positions −263 (SEQ ID NO 1, 2474) and −56 (SEQ ID NO 1, 2681), taking the first of the isolated cDNA 162 as the nucleotide +1 (in SEQ ID NO 1 the nucleotide +1 corresponds to nucleotide 2377), two possible TATA boxes, at positions −347 (SEQ ID NO 1, 2390) and −66 (SEQ ID NO 1, 2671), two putative CCAAT boxes, and at position −401 a CAAT box (SEQ ID NO 1, 2336) (FIG. 2) are found. In addition to these boxes, common to eukaryotic promoters, boxes typical of plant promoters have also been found. In Table 1 all the motifs of the plant promoters found between nucleotide −400 (SEQ ID NO 1, 1977) and +1 from the promoting region of END1 are defined using the database of the National Institute for Agro-biological Resources of Japan. We select this area on the basis that the distances at which the functional boxes are found in the promoters with respect to the start of transcription do not normally exceed 400 nucleotides according to references in the scientific literature on the different boxes studied.

Further analysis of the promoter region sequence allowed to detect the presence of other regulatory motifs. Two of them are CArG boxes ($^{-329}$TGAAAATACC$^{-320}$ (SEQ ID NO 1 $^{2408}$TGAAAATACC$^{2417}$) and $^{-300}$GGTTTCAACT$^{-291}$ (SEQ ID NO 1 $^{2437}$GGTTTCAACT$^{2446}$)), which, although not as similar as the first one to the consensus sequence, can also act as such. An example of CarG boxes that are functional, although differing from the consensus sequence, is represented by two of the three CarG boxes (CCTTTCATGG and CCATTTTTAG) of the promoter of the AP3 gene of *Arabidopsis* (Tilly J J et al., Development 125: 1647–1657, 1998). Other motifs that we have identified are $^{-290}$GTCAAAA$^{-284}$ (SEQ ID NO 1 $^{2447}$GTCAAAA$^{2453}$) present in the genes Zm13 and LAT52 (Zou J T et al., Am. J. Bot. 81: 552–561, 1994), the motif $^{-127}$ACGTCA$^{-122}$ (SEQ ID NO1 $^{2610}$ACGTCA$^{2615}$) localised on the gene Bp19 (Zou J T et al., Am. J. Bot. 81: 552–561, 1994] and the element $C(A)_{6/8}$ repeated three times (at positions −507 (SEQ ID NO:1, nucleotides 2230–2236), −288 (SEQ ID NO:1, nucleotides 2449–2457) and −247 (SEQ ID NO: 1, nucleotides 2490–2496)) on the promoters of the genes OlnB4 and OlnB19 [Hong H P et al., Plant Mol. Biol. 34: 549–555, 1997].

The different motifs found in the promoter region of END1 can be grouped in function of the type of genes where they have been described. The motifs SEF1, SEF4, E-box, RY and Element −300 are characterised by being present in gene promoters that code reserve proteins of the seed. The motifs GATA, GT1, I-box and ASF-1 are present in genes whose expression is regulated by light. The boxes that recognise factors homologous to Myb animal proteins: MYB-P, MYB-PH3 and MYB-ST1 have been found in genes implicated in the biosynthetic route of phenylpropanoids. The G-box motif is localised on a multitude of plant genes regulated by different environmental and physiological factors. SBF1 has been described on the defence gene chs15 of *Phaseolus vulgaris*. Rootmotif1 has been identified in the promoter sequence of two genes of root of corn rolD and pox1. And the elements GTCAAAA, ACGTCA and $C(A)_{6/8}$ are present in anther specific genes of Brassica

TABLE I

Description of the cis elements localised in the fragment lying between the nucleotides −400 and −1 of the promoter region of end1.

| MOTIF | POSITION (CHAIN) | CONSENSUS SEQUENCE | REFERENCE |
|---|---|---|---|
| ELEMENT −300 | −157 (+) | TGHAAARK | Thomas and Flavell, 1990 |
| AP3 | −209 (+) | TGTGGWWW | Mercurio and Karin, 1989 |
| ASF1 | −122 (−) | TGACG | Terzaghi and Cashmore, 1995 |
| G-BOX | −84 (+) | CACGTG | Foster et al., 1994 |
| E-BOX | −333, −295, −30 (+) | CANNTG | Kawagoe et al., 1994 |
| GATA | −265, −205 (+) | GATA | Gilmartin et al., 1990 |
| GT1 | −278, −156 (+) | GRWAAW | Lawton et al., 1991 |
| HEXMOTIF1 | −127 (+) | ACGTCA | Mikami et al., 1989 |
| I-BOX | −356 (−), −194 (−) | GATAA | Giuliano et al., 1988 |
| MYB-PH3 | −234 (+) | CNGTTA | Solano et al., 1995 |
| MYB-ST1 | −206 (+) | GGATA | Baranowskij et al., 1994 |
| ROOTMOTIF1 | −202 (+), −96 (+) | ATATT | Elmayan and Tepfer, 1995 |
| RY | −34 (+) | CATGCAY | Fujiwara and Beachy, 1994 |
| SIF | −215 (+) | ATGGTA | Zhou et al., 1992 |
| SEF1 | −392 (+) | ATATTTAWW | Lessard et al., 1991 |
| SEF4 | −276 (+) | RTTTTTR | Lessard et al., 1991 |
| MYB-P | −349 (+) | CCAACC | Grotewold et al., 1994 |
| SBF1 | −150 (+) | TTAA | Lawton et al., 1991 |
| CarG | −103 (−) | CC(A/T)$_6$GG | Shiraishi et al., 1993 |

*napus*, such as Bp19 [Zou J T et al., Am. J. Bot. 81: 552–561, 1994; Hong H P et al., Plant Mol. Biol. 34: 549–555, 1997]. All these motifs are indicated in SEQ ID NO 1.

Finally, the motif CArG is a DNA consensus sequence that is recognised by the MADS domain that characterises the homeotic genes of plants implicated in the development of floral organs [Huang H et al., Nuc. Acids Res. 21: 4769–4776, 1993; Shiraisi H et al., Plant J. 4: 385–398, 1993]. The genes APETALA-1 [AP]; Mandel M A et al., Nature 360: 273–277, 1992), APETALA-3 [AP3, Jack T et al., Cell 68: 683–697, 1992), PISTILLATA [P1, Goto K et al., Genes Dev. 8: 1548–1560, 1994) and AGAMOUS (AG, Yanofsky M F et al., Nature 346: 35–39, 1990] are homeotic genes that regulate the identity of the floral organs in *Arabidopsis*. These genes belong to the family of proteins containing a MADS domain in their sequence. The MADS domain is composed of 56 amino acids and is implicated in the dimerisation of the MADS genes with themselves or with other MADS genes and the subsequent binding to DNA of these dimers [Shore P and Sharrocks A D, E. J. Biochem. 229: 1–13, 1995].

The type B homeotic genes (AP3 and PI in *A. thaliana*) control the development of petals and stamens, and those of type C (AG in *A. thaliana*) control the formation of stamens and carpels. The END1 gene is expressed in stamens and, therefore, could be a target gene for the type B and C MADS genes. This hypothesis is supported by the existence of these putative CArG boxes in the promoter region of END1. Huang et al. [Nuc. Acids Res. 21: 4769–4776, 1993] and Shiraisi et al. [Plant J. 4: 385–398, 1993] determined that the AG gene would require some consensus sequences adjoining the CarG box for binding to DNA. The consensus sequence of binding to DNA for the MADS domain of AG was identified as: 5'-TT(A/T/G)CC(A/T)$_6$GG(A/T/C)AA-3' according to Shiraisi et al. [Plant J. 4: 385–398, 1993] and TT(A/T)CC(A/T)(A/t)$_2$(T/A)NNGG(-G)(A/t)$_2$ according to Huang et al. [Nuc. Acids Res. 21: 4769–4776, 1993]. The sequences adjoining the CArG box at position −103 in the promoter of END1, with the exception of two nucleotides, fit with those recognised by the MADS domain of the AGAMOUS gene elucidated by the previous authors (FIG. 3). This fact would confirm the hypothesis that END1 could be a direct target of a floral homeotic gene, specifically, it could be the target of the AGAMOUS gene.

Figure 4:
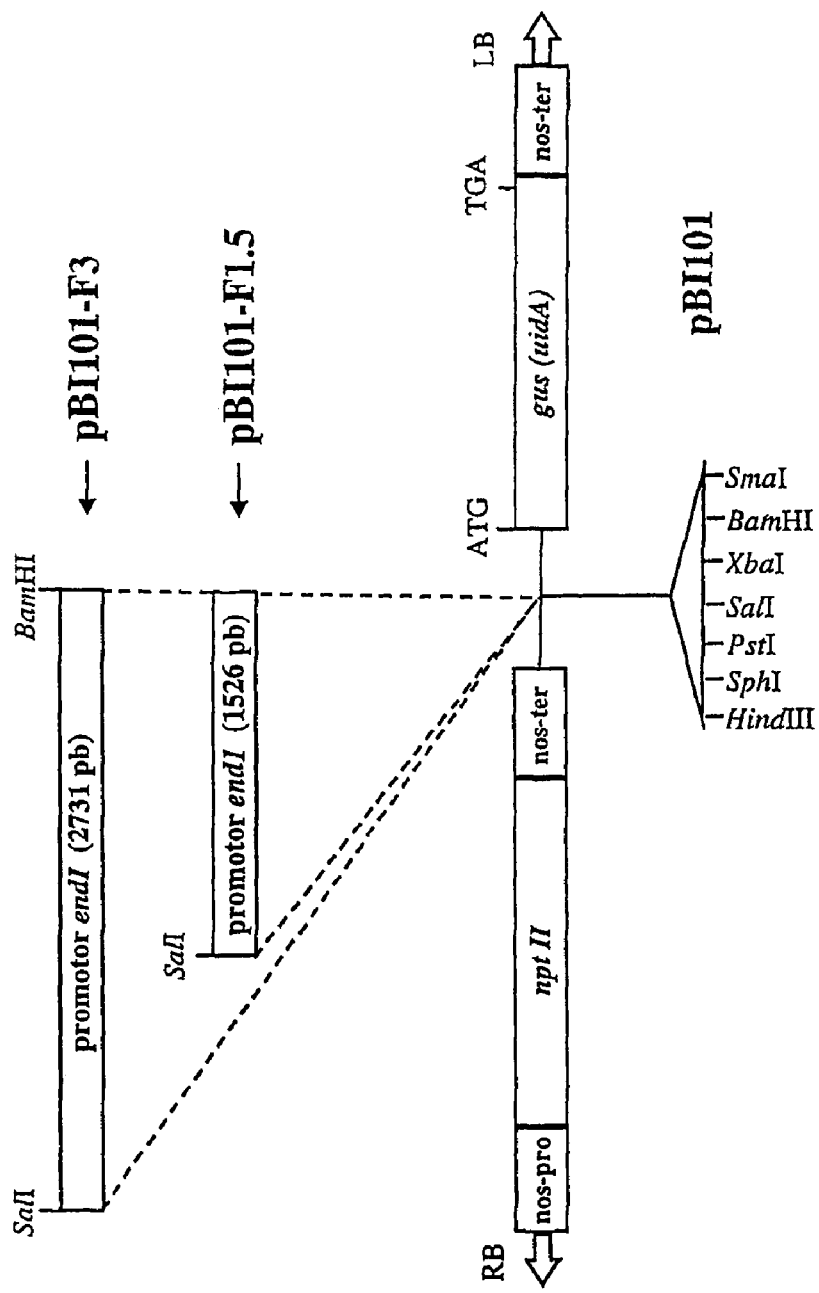
FIG. 4 shows a schematic representation of the pBI101-F3 and pBI101-F1.5 constructs used for transforming plants of *Arabidopsis*, tobacco and tomato. The plasmid pBI101 used for making the constructs consists of: the inherited promoter of nopaline synthetase (nos-pro) fused to the nptII gene which confers resistance to kanamycin, the uidA gene which codes for the enzyme b-glucuronidase (GUS-intron) and the polyadenylation signal of the nopaline synthetase gene (nos-ter) at the 3' extremes of both genes.

In order to confirm whether the promoting sequence cloned from END1 directed the specific expression of a gene in anthers and whether it was able to do so in plants other than the pea (*P. sativum*), we transformed tobacco plants (*Nicotiana tabacum*), *Arabidopsis thaliana* and tomato (*Lycopersicom sculentum*) with the promoter sequence fused to the coding sequence of the gene of b-glucuronidase (uidA, GUS-intron) [Example 1]. Two different constructs were carried out using the plasmid pBI101: pBI101-F3 and pBI101-F1.5 (FIG. 4). The first construct contains the nucleotide sequence comprised from nucleotide −2736 and −6 (SEQ ID NO 1, 1 to 2731) and the second one contains the sequence from the residue −1531 to −6 (SEQ ID NO 1, 1206 to 2731). This latter construct was assayed to mark, in an initial attempt, the sequence constituting the promoter region in the cloned fragment. Both constructs were introduced into *Arabidopsis* using strain C58 of *Agrobacterium tumefaciens*, and the construct pBI101-F3 into tobacco and tomato by means of the LBA4404 strain of *A. tumefaciens*. All these plants were transformed in turn with the plasmid pBI101 as a control and the expression of the reporter gene was subsequently analysed in different tissues.

The results of the transformations described in the previous examples show that the promoter sequence isolated from the END1 gene is fully functional as it directs the heterologous expression of a gene in a specific manner in anthers of plants other than the pea. Moreover, this capacity of the nucleotide sequence lying between position −1531 and −6 of the promoter (SEQ ID NO 4) has been described. On the other hand, the minimum nucleotide sequence that would substantially maintain this capacity for regulating specific expression in anthers can be defined with similar experiments. Thus, they form a part of the present invention all those nucleotide sequences, either of the complete region of the END1 promoter or any fragment thereof that substantially maintains this capacity for directing the specific expression in anthers. On the other hand, starting form this sequence of the promoter of the END1 gene of the pea, the promoter region of the two genes homologous with END1 can be obtained in other plant species thanks to the general knowledge available on molecular biology techniques. All these nucleotide sequences homologous with the one described in the present invention and which substantially maintain the capacity to regulate the specific expression in anthers form part of the present invention.

These regulatory sequences can be used in the development of DNA constructs that also include gene coding sequences of interest that in turn can be integrated into recombinant expression vectors. To do this, different techniques can be used that are well known in the state of the art [Sambrook et al, "Molecular cloning, a Laboratory Manual", 2$^{nd}$ ed., Cold Spring Harbor Laboratory Press, N.AND., 1989 Vol 1–3], some of which are shown in the present invention. These recombinant vectors allow the expression of different peptide, polypeptide, protein or RNA coding genes that, as described in the state of the art of the present invention, on being toxic for the tissues where they are expressed, would induce the ablation thereof and in this case would lead to androsterility of the resulting plant. Examples of these genes are those disclosed in the European patent application EP 412006 and which can be taken as a reference along with those described in the state of the art of the present invention. On the other hand, these constructs may contain other elements regulating the specific expression in anthers depending on the recombinant vector used, the plant to be transformed, etc. All these possible DNA constructs containing as the common dominator the nucleotide sequence of the invention as well as the use thereof for the production of androsterile plants form part of the present invention.

Therefore, the invention provides a DNA construct that comprises the nucleotide sequence of the invention and a coding nucleotide sequence for a peptide, polypeptide, protein, activity or RNA of interest. In a particular embodiment, said DNA construct comprises a coding sequence of activity promoting the sterility in plants under the control of the nucleotide sequence of the invention. In another particular embodiment, said DNA construct comprises a coding sequence of an activity that reverse or recovers the fertility of a plant, such as a coding sequence of an activity which is capable to inhibit the promoting activity of sterility in plants, under the control of the nucleotide sequence of the invention. Said DNA construct can also contain some regulatory elements, operationally linked, to the specific expression in anthers, for example, a terminal sequence of the transcription, depending on the recombinant vector used, the plant to be transformed, etc.

The sequence of nucleotides of the invention, or the DNA construct provided by this invention, can be inserted into an appropriate vector. Therefore, the invention also refers to a vector, such as an expression vector, that comprises said sequence of nucleotides of the invention, or said DNA construct. The choice of vector will depend on the host cell in which it is to be subsequently introduced. By way of example, the vector where said DNA sequence is introduced can be a plasmid or a vector that, when introduced into a host cell, is integrated into the genome of said cell and is replicated along with the chromosome (or chromosomes) in which it was integrated. To obtain said vector, conventional methods can be used that are well known to those skilled in the art [Sambrok et al., 1989, cited earlier].

The invention also provides a cell that comprises a nucleotide sequence of the invention, or a DNA construct containing said nucleotide sequence or said vector mentioned hereinabove. The host cells that can be transformed with the sequence of nucleotides of the invention can be prokaryotic cells or, preferably, eukaryotic cells, such as cells of plant tissue. The transformation of cells of plant tissue can also be carried out using conventional methods. For a review of the genetic transfer to plants, including vectors, methods of DNA transfer, etc, see for example the book titled "Ingeniería genética and transferencia génica", by Marta Izquierdo, Ed. Pirámide (1999), in particular, chapter 9, titled "Transferencia génica a plantas", pages 283–316.

The nucleotide sequence of the invention can be used for transforming plants and obtaining transformed plants. The transformation of plants is extensively described in the state of the art. As is well known, multiple systems can be used, for example, plasmid vectors, liposomes, electroporation, microinjection, diffusion, gene gun, co-precipitation with calcium phosphate, use of viral vectors, etc. In the present invention, the transformation of plants using a plasmid vector is described as an example of the many technical possibilities, all of which form a part of the present invention. In this sense, in Example 1, the transformation of tobacco plants (*N. tabacum*), tomato (*L. sculentum*) and *Arabidopsis thaliana* are described as examples of plant transformation.

The nucleotide sequence of the invention can be used to regulate the specific anther expression of a peptide, polypeptide, protein, activity or RNA sequence of interest in a plant. In a particular embodiment of the invention, the nucleotide sequence of the invention can be used to produce plants with male sterility (androsterility), that is, androsterile plants, which comprises transforming a plant with a DNA construct provided by this invention, said DNA construct comprising a coding sequence of an activity promoting sterility in plants, for example, the sequence of a cytotoxic gene, such as a gene that codes a ribonuclease activity, under the control of the nucleotide sequence of the invention, so that the expression of the coding sequence contained in said construct provokes the complete ablation of the anthers from very early developmental stages, preventing the formation of pollen therein and producing androsterility in the plant with 100% effectiveness. The resulting androsterile plant can be used for the production of hybrid seeds by means of a method comprising its culture under conditions that allow is development and maturing.

The invention also provides a method for restoring the fertility of an androsterile plant that comprises transforming said androsterile plant with a DNA construct comprising a coding sequence of an activity that reverses or restores the fertility under the control of the nucleotide sequence of the invention so that a fertile plant is obtained. In a particular embodiment of the invention, the androsterility is due to the expression of the barnase gene and the recovery of fertility is due to the expression of a sequence coding an activity that reverses or restores the fertility such as the expression of barstar, an activity able to. inhibit the ablation activity of. the anthers caused by BARNASE.

The plants susceptible to being transformed by the use of the nucleotide sequence of the invention can be both monocotyledonous plants and dicotyledonous plants, for example, monocotyledonous or dicotyledonous plants of agricultural interest, such as cereals, horticultural plants, e.g., tobacco, tomato, melon, watermelon, cucumber, etc.

In another particular embodiment, the invention provides a transgenic cell that comprises a nucleotide sequence of the invention integrated into its genome, as well as a transgenic plant comprising at least one of said transgenic cells. Said transgenic plants, which constitute an additional object of the invention, can be obtained by means of conventional techniques, for example, through the use of conventional antisense mRNA techniques and/or overexpression (in sense silencing) or others, for example, using binary vectors or other vectors available for the different plant transformation techniques currently in use. Examples of transgenic plants forming part of the present invention include both monocotyledon and dicotyledonous plants.

The nucleotide sequence of the invention is useful for obtaining androsterile plants and for producing hybrid seeds as it directs the expression of genes that code for certain enzymes that produce cellular ablation in those tissues that form the pollen sacs, as was explained earlier. This system, in combination with another similar one, which restores the fertility on producing an inhibitor of the enzyme used for provoking cellular ablation, would be of great utility in genetic improvement programmes based on the production of hybrids (heterosis). With an identical aim, different promoters had been tried before, but a 100% sterile plant population has not been attained with all of them [Zhan X et al., Sex. Plant Reprod.9: 35–43, 1996; Roberts M R et al., Sex. Plant Reprod. 8: 299–307, 1995]. This phenomenon is due to the fact that these promoters are activated in late stages of development when the pollen is already practically developed, so that the tissue that undergoes ablation (tapetum) is no longer strictly necessary for the pollen to reach full maturity. This methodology has a serious problem in that the final result obtained is a mixed population of hybrid and non-hybrid seeds. The nucleotide sequence of the invention constitutes an alternative to said promoters because it is activated when the differentiation of the staminal primordial cells is initiated. In this early phase, a proteinase or a nuclease would impede the correct development of the anther by destroying the cell lines that will give rise to tissues that form the pollen sacs at an early phase. The tissues where END1 is expressed are tissues that provide the support and the structure (architecture) for the anther, and so it is hard to imagine an anther able to produce pollen without these tissues. In this sense, Example 2 describes the production of androsterile plants of *A. thaliana* with a 100% efficacy. It is to be reasonably expected that the nucleotide sequence of the invention, in particular the END1 promoter, will be able to maintain its specificity in different plants, both dicotyledonous and monocotyledonous, as in several of these plants, the MADS genes of class C have been identified (homologous to AGAMOUS) which could activate said promoter like the dicotyledons, and so it is to be expected that said nucleotide sequence of the invention will be useful for producing androsterility, both in dicotyledonous plants and in monocotyledon plants of agricultural interest.

EXAMPLE 1

Functional studies of the END1 promoter in transgenic plants of *Arabidopsis thaliana*, tobacco (*Nicotiana tabacum*) and tomato (*Lycopersicom sculentum*)

1.1—Design of the pBI101-F3 and pBI101-F1.5 Constructs

The promoter region of the END1 gene was amplified, using the PCR technique, from the genomic fragment of DNA cloned in the pBluescript KS(+) plasmid, using the TB1, TB2 and TB3 oligos (Table 2). TB1 introduces a restriction site BamHI, and TB2 and TB3 introduce a restriction site SalI. Two fragments are amplified: one of 2731 bp containing almost all the isolated promoter region (−2736/−6) and another one of 1526 bp next to the coding region of the gene (−1531/−6 in FIG. 1) (SEQ ID NO 4). Neither of these two fragments contained coding sequence. Both fragments were cloned in the plasmid vector $PCR_{2,1}$. [Clar, J. M. (1998) Nuc. Acids. Res. 16:9677–9686; Mead, D., et al. (1991) Bio Technology 9:657–663]. Subsequently, the cloned inserts were released with the restriction enzymes BamHI and SalI, and were cloned in the plasmid pBI101 directing the expression of the gene uidA (GUS-intron) of b-glucuronidase (Vancanneyt G et al., Mol. Gen. Genet. 220:245–250, 1990). At the end of the process, two different constructs were attained: pBI101-F3 and pBI101-F1.5. The first one contained the fragment of 2731 bp and the second one the fragment of 1526 bp (FIG. 4).

TABLE 2

Primers used in the PCR amplifications.

| Primers | Sequence (5' ® 3') | DNA mould |
|---|---|---|
| TB1 | GAGAGCCTAGGAAGGTTATGTTGTGAGC | clone F3 |
| TB2 | GACTCGAGGTCGACTTCAACCTTATTAGTG | clone F3 |
| TB3 | GACTCGAGGTCGACAACCAGTGTGCATATATC | clone F3 |

The sequence TB1 is listed in the Sequence Listing as SEQ. I.D. NO. 5. The sequence TB2 is listed in the Sequence Listing as SEQ. I.D. NO. 6. The sequence TB3 is listed in the Sequence Listing as SEQ. I.D. NO. 7.

1.2.—Transformation of *Arabidopsis thaliana*, *Nicotiana tabacum* and *Lycopersicom sculentum*

In order to obtain the transgenic plants of tobacco, two cvs of *N. tabacum* were used: Samsun and Pettit Habane SRI. The transformation was conducted with leaf disks in co-culture with *A. tumefaciens* (strain LBA4404) for three days at 24° C. in darkness in MSS medium (Marashige and Skoog Medium 4.4 g/l, sucrose 2%, Mes 100 mg/l, phytagel 3.5 g/l, pH 5.9) following the method described by Horsch et al. (Science, 223: 496–498, 1984) with the modifications of Fisher and Guiltinan (Plant Mol. Biol. Reporter 13: 278–289, 1995). After incubation, the leaf disks were transferred to plates with regeneration and selection medium (MSS medium with IAA 0.2 mg/l, 6-BAP 2.2 mg/l, carbenicillin 400 mg/l and kanamycin 100 mg/l), and the buds that appeared were transferred to the rooting medium (MSS medium with IAA 0.2 mg/l, carbenicillin 200 mg/l and kanamycin 100 mg/l). The regenerated plants were transferred to pots with peat: vermiculite (1:1) where they were kept until they produced seeds. The culture conditions during the whole process were 12 h of light and a temperature of 24° C.

For the production of transgenic plants of *A. thaliana* the Columbia cv was used. The transformation protocol was followed by infiltration under vacuum and selection of the plants resistant to kanamycin described by Bechtold et al. (C R Acad. Sci. Paris, Life Sci., 316: 1194–1199, 1993). The strain C58 of *A. tumefaciens* was used. The plants resistant to kanamycin were transferred to pots with vermiculite: perlite: peat (1:1:1) and grown in culture chambers at 22° C. in long-day conditions until the seeds were finally collected.

In order to obtain transgenic tomato plants, the growth variety known as VC82b was used, following the method of Ellul et al., (Teor. Appl. Genet. In press, 2001) that uses cotyledons from germinating seeds (12 days) as starting material and the marker gene nptII to carry out selection of the transformants in a kanamycin medium.

1.3.—Histochemical Analysis (GUS) of the Transgenic Plants

The first generation of transformed plants was submitted to histochemical analysis of the activity of the b-glucuronidase gene. The studied tissues were infiltrated using two vacuum pulses of 5 min in a 0.1 M pH 7.0 phosphate buffer solution, 0.5 nM ferricyanide, 0.5 nM ferrocyanide, Triton X-100 at 0.1% and 2 mM X-G1cA acid and incubated in this solution at 37° C. for 16 hours. Afterwards, de-staining was carried out using successive washes with ethanol at 50°, 70° and 96°. GUS positive zones were identified as those coloured blue. The tissues that showed a blue coloration were fixed and included in paraffin (Cañas LA et al., Plant J. 6: 597–604, 1994) before being dehydrated, in order to identify by sections which types of cell in particular were responsible for b-glucuronidase activity. The photographs of the unprocessed tissues were taken with an MZ8 lens (Leica) and the tissue sections included in paraffin in an optical microscope Eclipse 600 (Nikon).

Analysis of Transgenic Plants of *Arabidopsis thaliana*

The study of the expression of the gene uidA (GUS-intron) was carried out by means of a histochemical assay of the b-glucuronidase activity in first generation tissues of transformed plants resistant to kanamycin. The organs assayed were: flowers, leaves, stems, roots and germinated seedlings.

Figure 5:
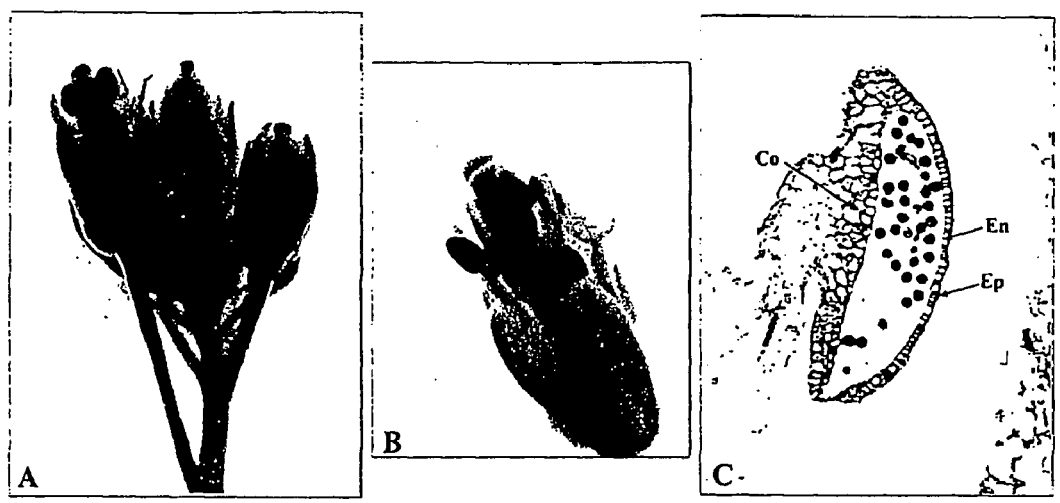
FIG. 5 shows the results of expression of the pea END1 promoter fused with the uidA gene (GUS-intron) in transgenic plants of *Arabidopsis thaliana*. A and B: After performing the corresponding histochemical assays of b-glucuronidase activity (GUS) with flowers in different developmental phases, said activity was only detected in the anthers (blue) and never in other floral organs or in the rest of the plant. C: Longitudinal section of a stamen with GUS activity included in paraffin. The GUS activity (blue) is detected in cells conforming the epidermis, the connective tissue and the endothecial tissue. No GUS activity was detected either in the tapetum or in the pollen. Although in the figure some grains of pollen appear blue, this is an artefact, as the blue colour only appears on the exine coating and never inside. Co: connective, En: endothecial, Ep: Epidermis.

We analysed 26 plants transformed with the pBI101-F3 construct, of which 24 showed specific b-glucuronidase activity and the remaining two did not shown any activity in any of the assessed tissues (FIG. 5). Of 19 plants transformed with the pBI101-F 1.5 construct and resistant to kanamycin, only two showed lack of GUS activity. In the remaining 17, blue coloration was observed specifically in anthers. The anther tissues that showed GUS activity were the same as those in which the END1 gene of pea is expressed: epidermis, connective, middle layer and endothecium. The staminal filament, the central vascular cylinder, nutritive tissue (tapetum), the pollen mother cells and the adult pollen did not show GUS activity in any case. The plants that were transformed with the pBI101 plasmid (negative control) did not show GUS activity in any of the analysed tissues.

No differences were observed in GUS activity between plants transformed with one or another construct. However, we observe variability in the intensity of coloration between flowers of the same plant, regardless of the construct used, since we can already distinguish flowers in a certain phase that did not show GUS activity and others in the same phase that did show GUS activity. Possibly, this phenomenon is due to the different degrees of penetration of the reagents of the assay in some tissues compared with others. The similarity of the results obtained with both constructs indicates that all regulatory sequences necessary for activity are to be found in the fragment comprised between residues −1531 and −6, although more study would be necessary to determine the minimum fragment able to maintain promoter activity.

1.5.—Analysis of the Transgenic Plants of Tobacco (*Nicotiana tabacum*)

The study of the expression of the uidA gene was carried out in the first generation of plants with the pBI101-F3 construct. The tissues that were assayed were: flowers, leaves, stems and roots.

Figure 6:
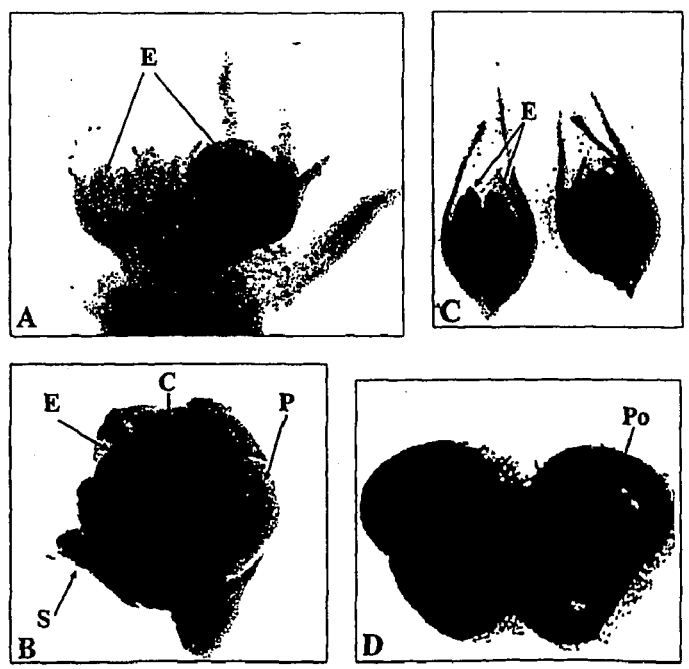
FIG. 6 shows the results of expression of the pea END1 promoter fused with the uidA gene (GUS-intron) in transgenic tobacco plants (*Nicotiana tabacum*). A, B and C: Histochemical assays of GUS activity in tobacco flowers in different development phases showing activity only in the anthers (blue). D: Fresh transversal section of an anther showing the pollen grains and the remaining tapetum tissue with no blue colouring. E: stamens, C: carpel, P: petals, S: sepals, Po: pollen.

We analysed 12 plants of tobacco resistant to kanamycin, of which 10 showed GUS activity in their anthers and two did not show any activity in the tissues assayed (FIG. 6). We found the same variability in blue coloration between plants from the same plant as observed in *A. thaliana*. The plants transformed with the pBI101 plasmid (negative control) did not show b-glucuronidase activity in any of the tissues as expected.

1.6.—Analysis of Transgenic Plants of Tomato (*Lycopersicom sculentum*)

Figure 7:
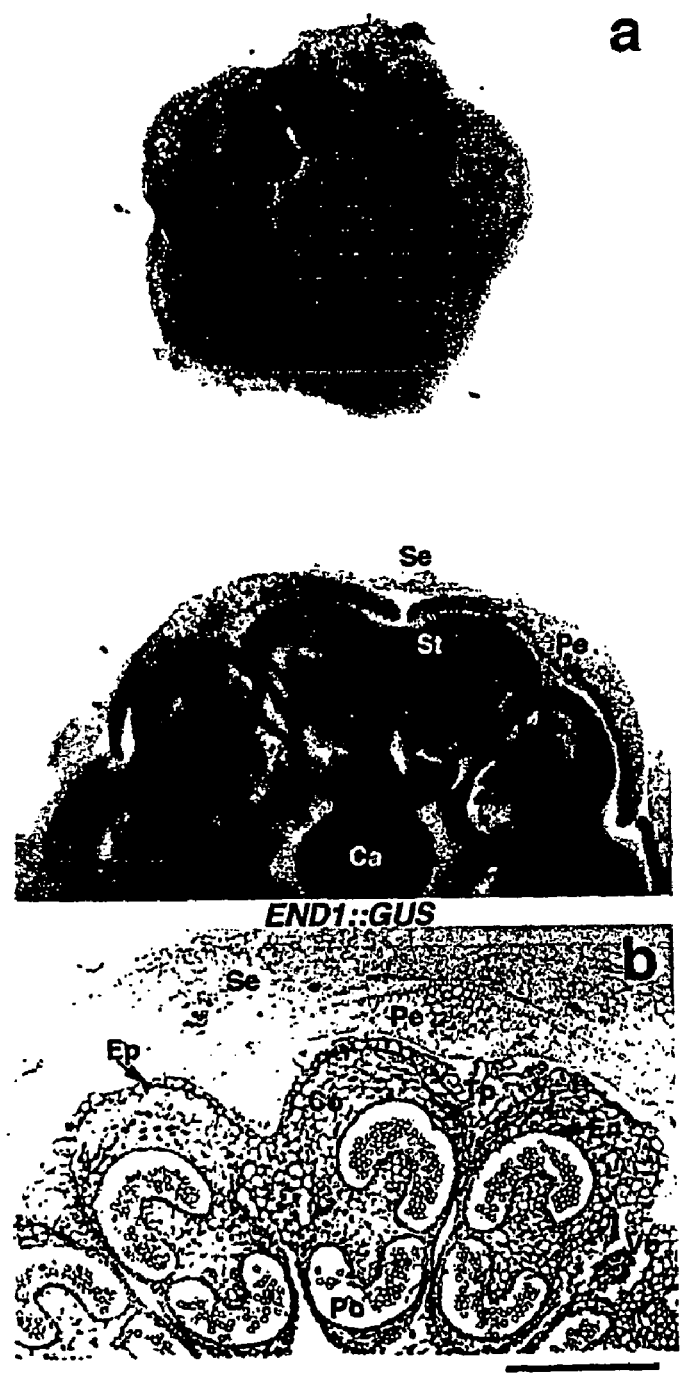
FIG. 7 shows the results of expression of the pea END1 promoter fused with the uidA gene (GUS-intron) in transgenic tomato plants (*Lycopersicom sculentum*). a: Histochemical assays of GUS activity in tomato flowers showing activity specifically in the anthers (St). b: Section in paraffin of one of these flowers, the GUS activity is restricted to tissues that form the pollen sacs (epidermis, endothecium, connective, etc) but do not exist in the tapetum or in the pollen. Se: sepals, Pe: petals, St: stamens. Ca: carpel, Ep: epidermis, Co: connective, En: endothecium, Tp: tapetum and Po: pollen.

10 different lines of plants resistant to kanamycin were analysed, of which, half turned out to be positive when expression of the uidA gene in anthers was analysed. Study of the expression of said gene was carried out in the first generation of plants transformed with the pBI101-F3 construct. The tissues assayed were: flowers, leaves, stems and roots. As in previous cases, the results were practically identical, observing the expression of the GUS gene only in those tissues that form the pollen sac of the anther (FIG. 7).

EXAMPLE 2

Production of androsterile plants of *Arabidopsis thaliana* using the barnase gene under the control of the END1 promoter 2.1.—Design of the Construct pBI101-pEND1-barnase/barstar The pBI101-F3 construct that contains fragment 2731 bp of the END1 promoter and the GUS gene, was digested with the BamHI and SacI restriction enzymes, to give rise to the release of the GUS fragment. The fragment corresponding to the pBI101-pEND1 plasmid with BamHI and SacI termini was isolated on agarose gel using the Quiaex II system (Quiagen). The barnase/barstar fragment (Mariani et al., Nature 347: 737–741, 1990; Mariani et al., Nature 357: 384–387, 1992), cloned at the BamHI site of the plasmid pBluescript KS(+), was amplified using the oligos:

```
T7:       5' TAATACGACTCACTATAGGG 3', e
          (SEQ. I.D. NO. 8)

Inhi II:  5' GCGAGCTCTTAAGAAAGTATGATGGTGATG 3'
          (SEQ. I.D. NO. 9)
```

With the first, the splicing site BamHI is maintained at the level of the ATG of the barnase gene and the later creates a splicing site for SacI at the level of the stop codon of the barstar gene. The fragment product of the PCR reaction was bound to the pGEM-T vector (Promega). Finally, the cloned barnase/barstar insert (918 bp) was released with BamHI and SacI and bound to the pBI101-pEND1 plasmid with BamHI and SacI termini.

2.2.—Results and Comments

Figure 8:
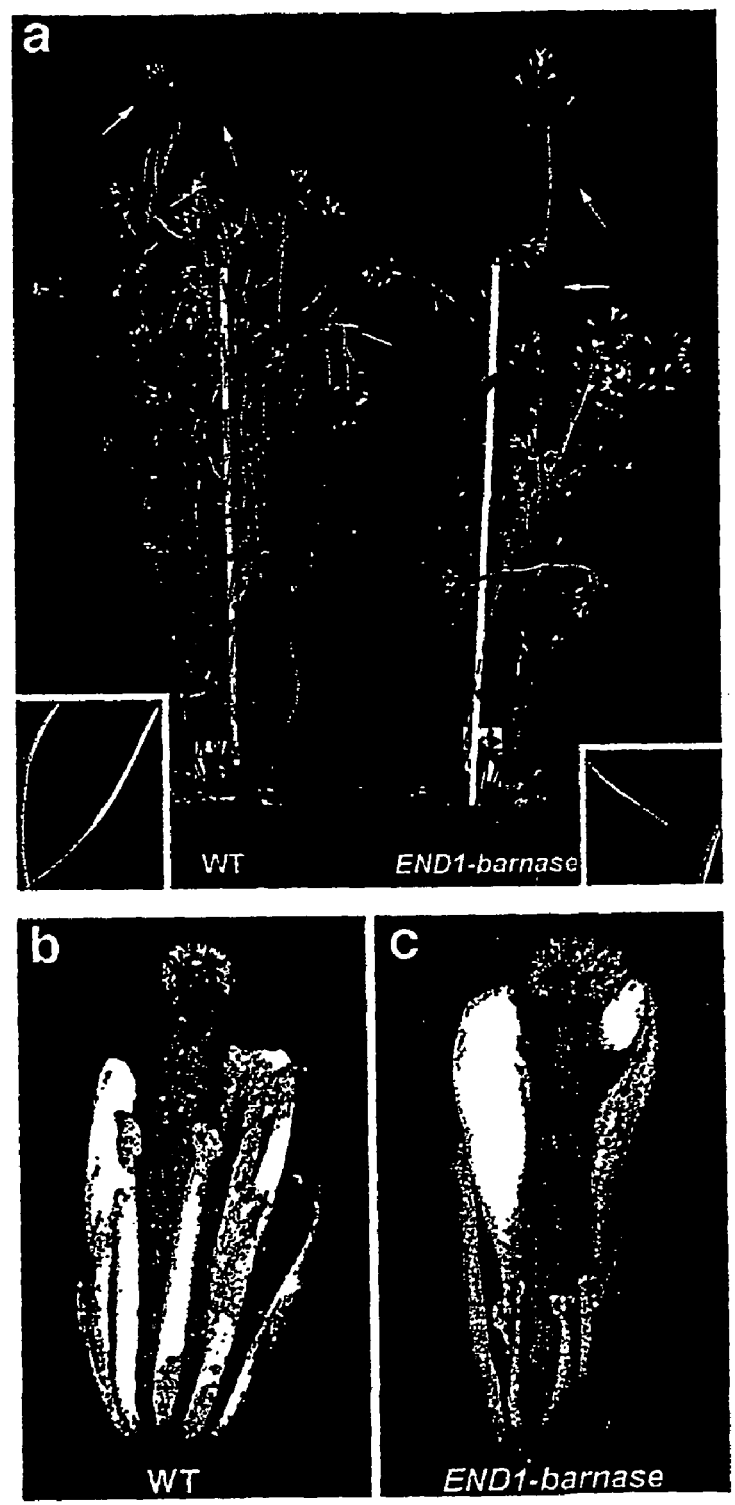
FIG. 8 shows the results of transgenic *Arabidopsis thaliana* plants with male sterility by using the BARNASE gene directed by the END1 promoter. a: Control plant of *Arabidopsis* (WT) showing the siliques (arrows, right box) formed as a result of the fertilisation of its ovaries with mature pollen. Beside it, a transgenic plant can be seen in which the effects of expression of the barnase gene under the control of the END1 promoter is shown: The ageing ovaries (right box) remain in the plant as they have not been pollinated (arrows). b: Normal flower of a wild type plant of Arabidopsis after pollination of the stigma by means of dehiscence of the anthers (phase 14). After the maturing process of the anther, the filament has undergone a lengthening until the pollen sacs are located at the height of the stigma to facilitate their pollination. c: Flower of a transgenic plant in the same state showing the BARNASE effects on the development of the anther. The ablation of the anther is complete, with no pollen sacs being formed. The filament does not undergo the lengthening process, as the development of the anther is not completed. In these conditions, pollination is impossible and the plant is 100% sterile.

The results obtained are shown in FIG. 8. The plants transformed with the pEND1-BARNASE construct showed how the carpels of their flowers are not fertilised and do not form the corresponding siliques as occurs in the control plant. On the other hand, the flowers of the transgenic plants showed the filaments that have not lengthened and at whose end there appear some very rudimentary structures instead of anthers. The total of 17 transgenic plants resistant to kanamycin recovered showed a complete ablation of their anthers and therefore, 100% male sterility.

Figure 9:
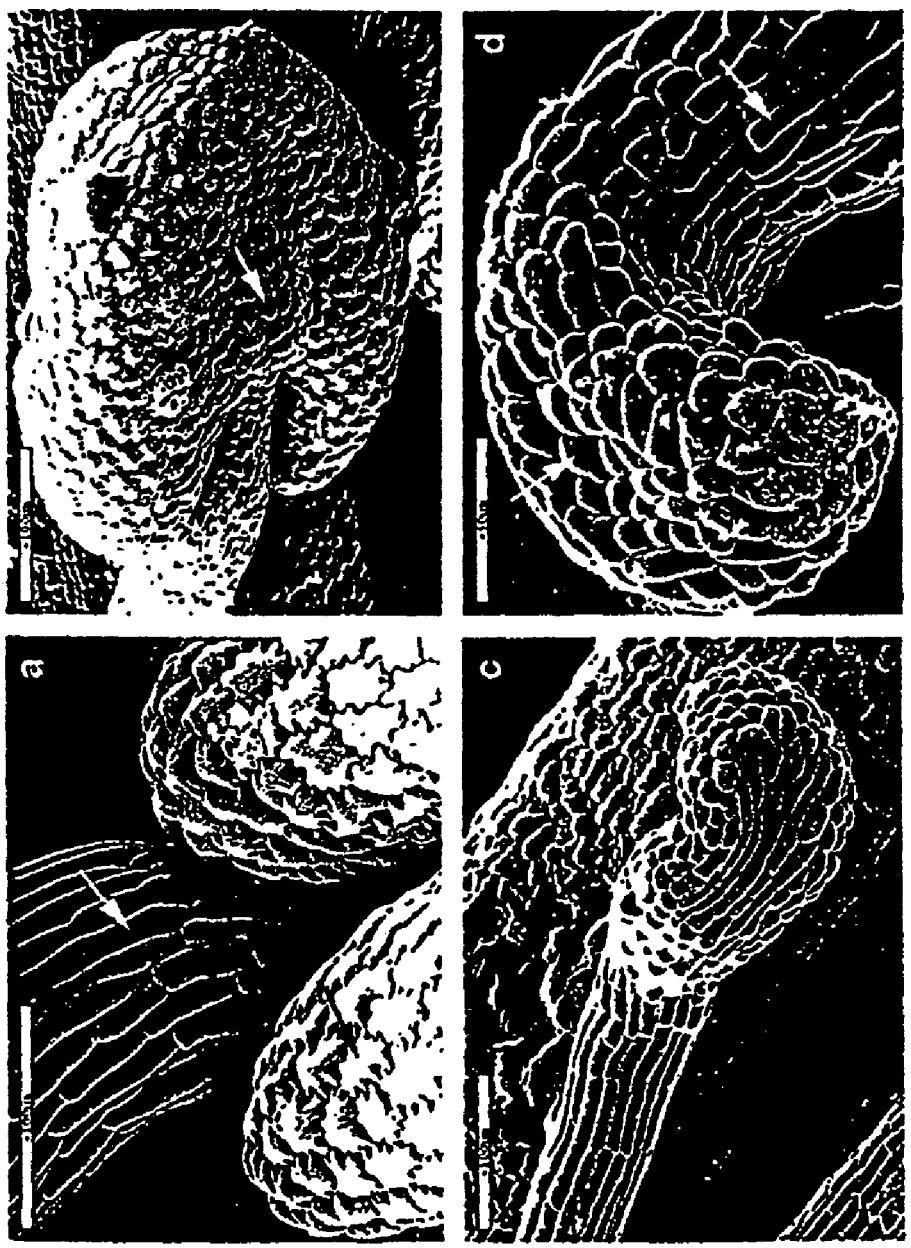
FIG. 9 shows the result of studies by means of a scanning electron microscope (SEM) of the cell types present in the structures formed in the place of the anthers of transgenic plants bearing the pEND1-barnase construct. a: Stamen of a control flower of *Arabidopsis*. The black arrow indicates the cell types present in the epidermis of the anther (saw-tooth edges) and the black one indicates those of the filament (lengthened). b: The same stamen seen from the opposite side. A change in cell type is observed (more rounded) in the area where the filament reach the anther (arrow). c: Stamen of a transgenic plant, the cell types present in the filament are observed and the rounded ones at the insertion zone, but not those of the epidermis of the pollen sacs. d: Detail of the structure present in the terminal zone of the filament in which the lengthened cell types of the filament coexist with the rounded types of the insertion zone.
Figure 10:
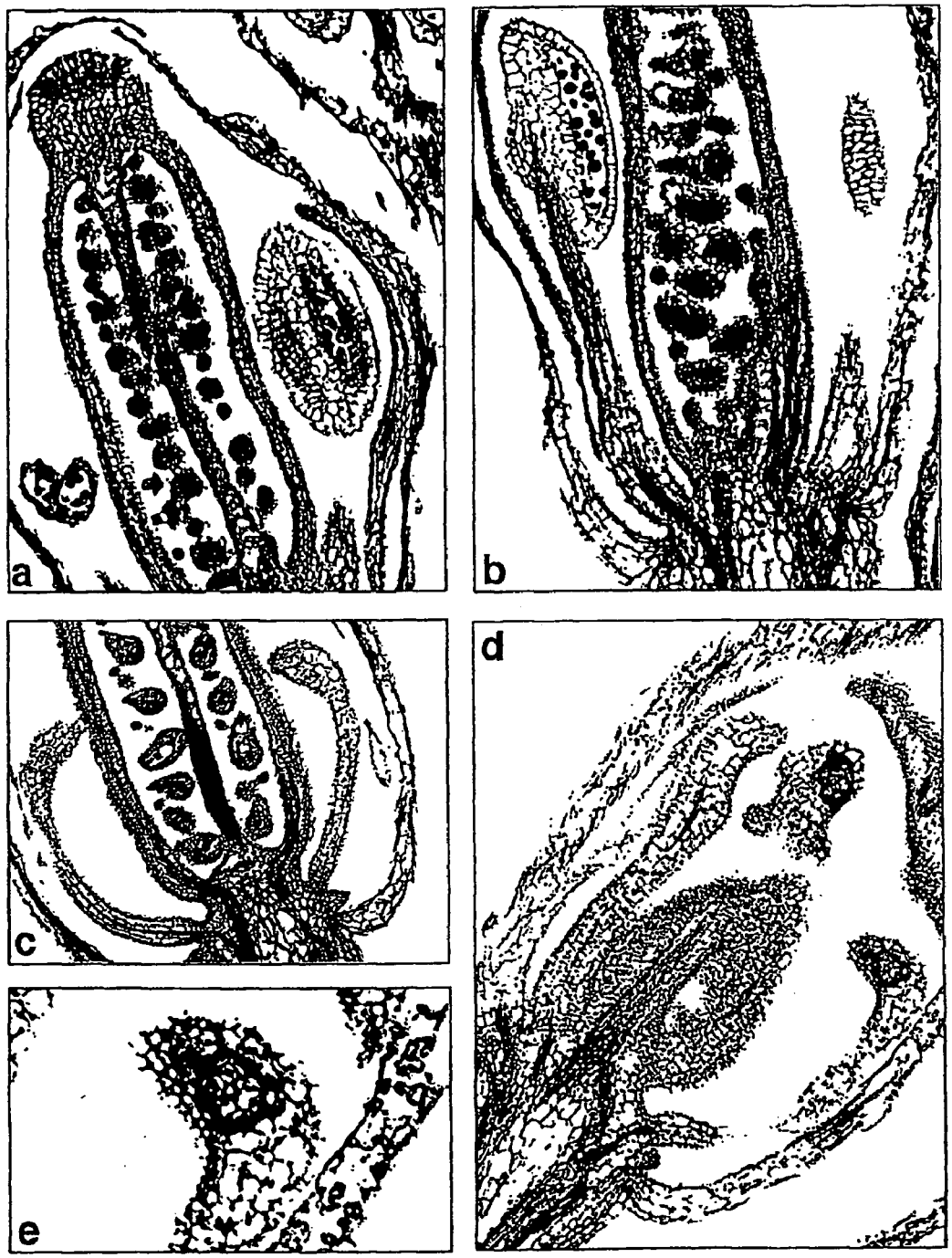

The studies carried out with a scanning electron microscope (SEM) showed (FIG. 9) that the cell types present in said structures do not correspond to those present in the epidermis of an anther, detecting only those that form the filament or those that are present at the zone where the filament joins the anther. These studies were completed with sections of structures in paraffin with subsequent staining thereof with Alcian blue and Safranin to detect cell lines related to the development of the pollen. In FIG. 10, we see how small groups of mother cells of pollen and perhaps of external tapetum (in red) are observed in the interior of the structures located at the end of the filament. These cells seem to have stopped their development on comparing them with the process that normally produces an untransformed anther.

As has already been explained, the barnase/barstar system has been successfully used in the production of plants with male sterility because it is directed towards the anthers of the plant by means of the use of specific promoters (generally of tapetum). The main disadvantage of this system lies in the use of said promoters, which act too late in the development of the anther and on a tissue (tapetum) implicated in the nutrition of the cells that will give rise to the pollen. This effect leads to the production to a certain extent of pollen in some flowers of the plant, causing escapes from the system with the corresponding loss in effectiveness (<95%).

Using the promoter of the END1 gene these problems do not exist due to three reasons:

The expression of BARNASE (RNase) is carried out in very early developmental phases, leading to complete ablation of the cell lines that will give rise to the tissues that form the pollen sacs: epidermis, endothecium, connective, middle layer, etc.

Only the filament is formed at the base of the anther and this never lengthens to reach the stigma of the carpel.

Although the cell lines that will give rise to external tapetum and to pollen mother cells do not experience the effects of BARNASE as they are not a target for the END1 promoter, they stop in an early phase of their development as they do not have the support of the remaining tissues of the anther, which would also be fundamental for the process of mature pollen release (dehiscence).

We claim:

1. An isolated nucleotide sequence regulating the specific expression in anthers of a gene selected from the group consisting of:
    a nucleotide sequence comprising the nucleotide sequence shown in SEQ ID NO:1; and
    a nucleotide sequence comprising the nucleotide sequence shown in SEQ ID NO:4.

2. A DNA construct comprising the nucleotide sequence according to claim 1, operably linked to a nucleic acid encoding a peptide or RNA.

3. A recombinant vector comprising the nucleotide sequence of claim 1.

4. A host cell comprising the nucleotide sequence of claim 1, the DNA construct of claim 2, or the recombinant vector of claim 3.

5. A plant transformed with the nucleotide sequence of claim 1, the DNA construct of claim 2, or the recombinant vector of claim 3.

6. A plant transformed with the DNA construct of claim 2, wherein expression of said peptide or RNA induces ablation of an anther of said plant.

7. The plant of claim 5, wherein said plant is selected from the group consisting of a monocot and a dicot.

8. A method for producing hybrid seeds, said method comprising the steps of:
    transforming a plant with a DNA construct comprising the nucleotide sequence of claim 1 operably linked to a coding sequence encoding a protein or RNA that confers sterility to plants wherein expression of said coding sequence results in ablation of anthers of said plant, thereby producing an androsterile plant; and
    crossing said androsterile plant with an isogenic and fertile plant to obtain hybrid seeds.

9. A method for producing androsterile plants, said method comprising the steps of:
    transforming a plant with a DNA construct comprising the nucleotide sequence of claim 1 operably linked to a coding sequence encoding a protein or RNA that confers sterility to plants wherein expression of said coding sequence results in ablation of anthers of said plant.

10. A method for restoring fertility of an androsterile plant, said method comprising the steps of:
    transforming an androsterile plant with a DNA construct comprising the nucleotide sequence of claim 1 operably linked to a coding sequence encoding a protein or RNA that that reverses or restores fertility in said plant.

* * * * *